United States Patent [19]

Hamprecht et al.

[11] 4,315,766
[45] Feb. 16, 1982

[54] 4H-3,1-BENZOXAZINE DERIVATIVES

[75] Inventors: Gerhard Hamprecht, Weinheim; Bruno Wuerzer, Otterstadt, both of Fed. Rep. of Germany

[73] Assignee: BASF Aktiengesellschaft, Fed. Rep. of Germany

[21] Appl. No.: 138,414

[22] Filed: Apr. 8, 1980

[30] Foreign Application Priority Data

Apr. 12, 1979 [DE] Fed. Rep. of Germany ....... 2914915

[51] Int. Cl.³ .................... A01N 43/86; C07D 265/22
[52] U.S. Cl. .......................................... 71/88; 71/86; 71/87; 71/90; 71/91; 71/92; 71/93; 71/94; 71/95; 544/92
[58] Field of Search ................. 544/92; 71/28, 90, 92, 71/93, 88

[56] References Cited

U.S. PATENT DOCUMENTS

| | | | |
|---|---|---|---|
| 3,232,736 | 2/1966 | Seefelder et al. | 71/88 |
| 3,357,977 | 12/1967 | Errede | 544/92 |
| 3,740,402 | 6/1973 | Cevasco | 544/92 |
| 3,748,327 | 7/1973 | Beyerle et al. | 544/92 |
| 3,914,121 | 10/1975 | Doyle, Jr. | 544/92 |
| 3,970,652 | 7/1976 | Doyle, Jr. | 71/88 X |
| 3,989,698 | 11/1976 | Jacobs et al. | 544/92 |

FOREIGN PATENT DOCUMENTS

| | | | |
|---|---|---|---|
| 269985 | 3/1965 | Australia | 544/92 |
| 648259 | 4/1964 | Belgium . | |
| 1670375 | 11/1970 | Fed. Rep. of Germany . | |
| 2241012 | 3/1973 | Fed. Rep. of Germany . | |
| 2556590 | 9/1976 | Fed. Rep. of Germany . | |
| 2121341 | 1/1971 | France . | |

OTHER PUBLICATIONS

C.A., 74 (1971), 53689r, Eckroth, et al.
C.A., 74 (1971), 53682h, Schmidt, et al.

Primary Examiner—Joseph Paul Brust
Attorney, Agent, or Firm—Keil & Witherspoon

[57] ABSTRACT 4H-3,1-Benzoxazine derivatives of the formula

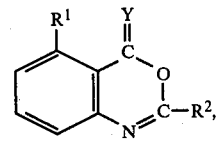

where $R^1$, $R^2$ and Y have the meanings given in the specification, and their use for controlling unwanted plant growth in numerous crops, such as cereals, Indian corn, soybeans and cotton.

10 Claims, No Drawings

4H-3,1-BENZOXAZINE DERIVATIVES

The present invention relates to 4H-3,1-benzoxazine derivatives, herbicides containing these compounds as active ingredients, and a process for controlling undesired plant growth with these compounds.

Substituted 4H-3,1-benzoxazin-4-ones are known as intermediates for the synthesis of drugs (German Laid-Open Applications DOS Nos. 1,670,375 and 2,556,590) and as herbicidal active ingredients; in particular, 4H-3,1-benzoxazin-4-ones which carry an unsubstituted or substituted phenyl radical in the 2-position are herbicidally active (Belgian Pat. No. 648,259 and U.S. Pat. Nos. 3,970,652 and 3,914,121). The known compounds are well tolerated by a number of crops, eg. species of grain, rice, Indian corn and sorghum. Their shortcomings reside in a narrow spectrum of action on broad-leaved weeds. Furthermore, even in the case of plants which these benzoxazines control effectively, relatively large amounts per unit area must be used.

We have found that 4H-3,1-benzoxazine derivatives of the formula I

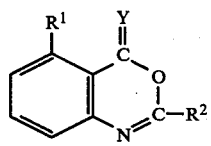 (I), where
Y is oxygen or sulfur,
$R^1$ is hydrogen, halogen, nitro, alkyl, haloalkyl, haloalkoxy or haloalkylmercapto, each of 1 to 4 carbon atoms, cyano, thiocyano, $CO_2R^3$,

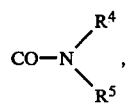

$Y'R^4$, $SOR^4$, $SO_2R^4$, $SO_2OR^4$,

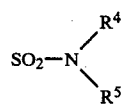

or $CO-R^4$, where
$R^3$ is alkyl or alkenyl of up to 4 carbon atoms,
$R^4$ is alkyl of 1 to 4 carbon atoms,
$R^5$ is hydrogen or alkyl of 1 to 4 carbon atoms,
$Y'$ is oxygen or sulfur and
$R^2$ is a cycloaliphatic or bicycloaliphatic radical of 3 to 10 carbon atoms which is monosubstituted or polysubstituted by methyl, or is a pyrimidine, pyrazine, pyridazine, triazine, thiazole, isothiazole, pyrazole, imidazole, triazole, oxazole or isoxazole radical which is unsubstituted or is monosubstituted or polysubstituted by methyl and/or halogen, or is a furan, morpholine or pyridine radical which is monosubstituted or polysubstituted by methyl and/or halogen, and, if $R^1$ is hydrogen, $R^2$ may also be an m-substituted or p-substituted, or m- and p-substituted, aryl radical of the formula $Ar(R^6)_n$, where Ar is phenyl and $R^6$ is alkylmercapto, haloalkoxy, haloalkylmercapto, alkylsulfinyl, haloalkylsulfinyl, alkylsulfonyl or haloalkylsulfonyl, each of 1 to 4 carbon atoms,

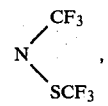

alkoxycarbonyl, alkenyloxycarbonyl, alkylmercaptocarbonyl or alkenylmercaptocarbonyl, each with alkyl or alkenyl of 1 to 4 carbon atoms, $NH-CO-NH-CH_3$, $NH-CO-N(CH_3)_2$,

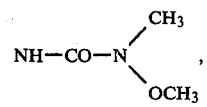

formamido, alkoxycarbamyl, alkenyloxycarbamyl, alkylmercaptocarbamyl, alkenylmercaptocarbamyl, alkylmercaptodithiocarbamyl, alkenylmercaptodithiocarbamyl, alkylcarbamido, dialkylcarbamido, alkenylcarbamido, dialkenylcarbamido, alkylsulfamyl, dialkylsulfamyl, alkylsulfonamido or haloalkylsulfonamido, each with alkyl or alkenyl of 1 to 4 carbon atoms, or formyl, and n is 1 or 2, and if $R^1$ does not denote hydrogen or halogen, $R^6$ may also denote hydrogen, halogen, cyano, thiocyano, nitro, haloalkyl of 1 to 4 carbon atoms or acyl of 2 to 5 carbon atoms, and if $R^1$ denotes fluorine or hydrogen and n is 2, $R^6$ may also denote hydrogen, fluorine, chlorine, nitro or alkoxycarbonyl of 2 to 5 carbon atoms, and if $R^1$ denotes halogen and n is 1, $R^6$ may also denote haloalkoxy, haloalkylmercapto or alkylsulfinyl, and if $R^1$ denotes hydrogen, $R^2$ may also be aralkyl substituted in the m-position or p-position or m- and p-position, by haloalkyl or haloalkoxy, each of 1 to 4 carbon atoms, are excellently tolerated by crop plants and exhibit a substantially more powerful herbicidal action than the benzoxazines hitherto disclosed.

In formula I, $R^1$ is, for example, hydrogen, fluorine, chlorine, bromine, iodine, nitro, methyl, ethyl, isopropyl, n-propyl, n-butyl, isobutyl, tert.-butyl, trichloromethyl, difluorochloromethyl, trifluoromethyl, difluoromethyl, 2,2,1,1-tetrafluoroethyl, trifluoromethoxy, hexafluoroisopropoxy, difluoromethylmercapto, trifluoromethylmercapto, a radical of the formula $Y''CF_2C(Z)_3$, where $Y''$ is oxygen or sulfur and each Z independently may be hydrogen, fluorine, chlorine, bromine or iodine, eg. 2,2,1,1-tetrafluoroethoxy, 1,1-difluoroethoxy, 2,2,1,1-tetrafluoroethylmercapto and 1,1-difluoroethylmercapto, cyano, thiocyano, $CO_2CH_3$, $CO_2C_2H_5$, $CO_2-CH(CH_3)_2$, $CO_2-CH_2-CH=CH_2$, $CO-N(CH_3)_2$, $CO-N(C_2H_5)_2$, methoxy, ethoxy, n-butoxy, isobutoxy, methylthio, ethylthio, n-propylthio, sec.-butylthio, $SOCH_3$, $SOC_2H_5$, $SO_2CH_3$, $SO_2C_2H_5$, $SO_2C_3H_7$, $SO_2OCH_3$, $SO_2OC_2H_5$, $SO_2OC_4H_9$, $SO_2-NHCH_3$, $SO_2-N(CH_3)_2$, $SO_2-N(C_2H_5)_2$, formyl, acetyl and propionyl.

$R^2$ in formula I is, for example, cyclopentyl, cyclohexyl, α-, β- or γ-methylcyclopentyl, α-, β- or γ-methylcyclohexyl, 1,4-methano-bicyclo-(4,3)-nonane, 2-methyl-fur-3-yl, 3-methyl-fur-2-yl, 4-methyl-fur-2-yl, 5-methyl-fur-2-yl, 2-methyl-fur-4-yl, 3-methyl-fur-4-yl, 2,5-dimethyl-fur-4-yl, 4-methyl-pyrid-2-yl, 5-methyl-pyrid-2-yl, 2-methyl-pyrid-4-yl, 2-methyl-pyrid-5-yl, 3-chloro-pyrid-5-yl, 2-chloro-pyrid-4-yl, 2-chloro-pyrid-5-yl, pyrimidin-2-yl, -4-yl, -5-yl or -6-yl, 4-methyl-pyrimidin-2-yl, 4-chloropyrimidin-2-yl, pyridazin-3-, -4-, -5- or -6-yl, imidazol-1-, -2-, -4- or -5-yl, 5-methyl-imidazol-2-yl, 2-methyl-imidazol-5-yl, oxazol-2-, -4- or -5-yl, 2-methyl-oxazol-5-yl, isoxazol-3-, -4- or -5-yl, 3-methyl-isoxazol-5-yl, 3-chloro-isoxazol-5-yl, 1,2,4-triazol-1-yl, 1,2,5-triazin-3-yl, 1,2,5-triazin-4-yl, 1,2,4-triazol-3-yl, 1,2,4-triazolyl-5-yl, α-pyrazinyl or aryl, especially phenyl which may be substituted by the following in the m-position, p-position or m- and p-position: methylmercapto, ethylmercapto, isopropylmercapto, chloromethoxy, fluoromethoxy, difluoromethoxy, difluorochloromethoxy, trifluoromethoxy, trichloromethoxy, 1,1,2,2-tetrafluoroethoxy, 1,1,2-trifluoro-2-chloroethoxy, 1,1,1-trifluoro-2-bromoethoxy, 1,1,2,3,3,3-hexafluoro-n-propyloxy, pentafluoroethoxy, hexafluoroisopropoxy, difluoromethylmercapto, trifluoromethylmercapto, pentafluoroethylmercapto, 1,1,2,2-tetrafluoroethylmercapto, trichloromethylmercapto, dichlorofluoromethylmercapto, trifluoromethylmercapto, CH$_3$SO$_2$, C$_2$H$_5$SO$_2$, i—C$_3$H$_7$SO$_2$, ClCH$_2$SO$_2$, F$_2$CHSO$_2$, CF$_3$SO$_2$, CF$_3$CF$_2$SO$_2$,

CO$_2$CH$_3$, CO$_2$C$_2$H$_5$, CO$_2$—i—C$_3$H$_7$, CO$_2$—n—C$_4$H$_9$, CO$_2$—CH$_2$CH=CH$_2$, CO—SCH$_3$, CO—SC$_2$H$_5$, CO—S—i—C$_3$H$_7$, CO—S—CH$_2$—CH=CH$_2$, NH—CO—NHCH$_3$, NH—CO—N(CH$_3$)$_2$,

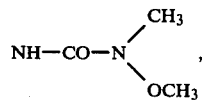

NH—CHO, NH—COOCH$_3$, NH—COOC$_2$H$_5$, NH—COO—i—C$_3$H$_7$, NH—COO—sec—C$_4$H$_9$, NH—COOCH$_2$—CH=CH$_2$, NH—CO—SCH$_3$, NH—CO—SC$_2$H$_5$, NH—CO—S—i—C$_3$H$_7$, NH—CO—S—CH$_2$—CH=CH$_2$, NH—CS—SCH$_3$, NH—CS—SC$_2$H$_5$, NH—CS—S—i—C$_3$H$_7$, NH—C-S—S—CH$_2$—CH=CH$_2$, CO—NHCH$_3$, CO—NHC$_2$H$_5$, CO—NH—i—C$_3$H$_7$, CO—N-H—sec—C$_4$H$_9$, CO—NH—CH$_2$—CH=CH$_2$, CO—N(CH$_3$)$_2$, CO—N(C$_2$H$_5$)$_2$, CO—N(i—C$_3$H$_7$)$_2$, CO—N(CH$_2$—CH=CH$_2$)$_2$, SO$_2$—NHCH$_3$, SO$_2$—NHC$_2$H$_5$, SO$_2$—NH(i—C$_3$H$_7$), SO$_2$—N(CH$_3$)$_2$, SO$_2$—N(C$_2$H$_5$)$_2$, NH—SO$_2$—CH$_3$, NH—SO$_2$—C$_2$H$_5$, NH—SO$_2$—CF$_3$, NH—SO$_2$—NHCH$_3$, NH—SO$_2$—NHC$_2$H$_5$, CHO, fluorine, chlorine, bromine, iodine, cyano, thiocyano, nitro, acetyl, propionyl, trifluoromethyl, difluorochloromethyl, difluoromethyl or 1,1,2,2-tetrafluoroethyl, or aralkyl, eg. benzyl, which may be substituted in the m-position or p-position or m- and p-position, for example by trifluoromethyl or trifluoromethoxy.

Preferred compounds of the formula I are those where R$^1$ is hydrogen, R$^2$ is substituted phenyl, R$^6$ is haloalkoxy, haloalkylmercapto or alkylsulfinyl, each of 1 to 4 carbon atoms, and n is 1, or where R$^1$ is halogen, R$^2$ is substituted phenyl, R$^6$ is haloalkoxy, haloalkylmercapto or alkylsulfinyl, each of 1 to 4 carbon atoms, and n is 1, those where R$^1$ is hydrogen, R$^2$ is substituted phenyl, R$^6$ is halogen, haloalkoxy, haloalkylmercapto or alkylsulfinyl, each of 1 to 4 carbon atoms, and n is 2, or those where R$^1$ is fluorine, R$^2$ is unsubstituted or substituted phenyl, R$^6$ is hydrogen or halogen and n is 2.

Further, we have found that benzoxazine derivatives of the formula I are obtained if an unsubstituted or substituted anthranilic acid of the formula II

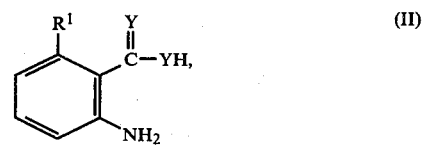

where R$^1$ and Y have the above meanings, is reacted with a twofold or even higher molar excess of a carboxylic acid halide of the formula III

where R$^2$ has the above meanings and Hal is halogen, especially fluorine, chlorine or bromine, in an aromatic tertiary amine as the solvent, at from 10° to 60° C.

If 3-nitro-4-chloro-benzoyl chloride and anthranilic acid are used as starting materials, the course of the reaction may be represented by the following equation:

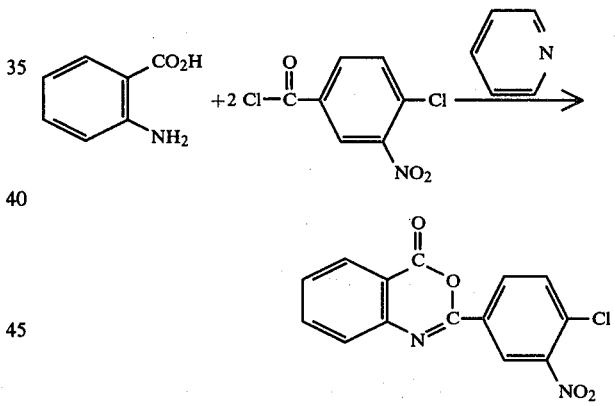

Advantageously, a twofold molar excess of the carboxylic acid halide of the formula III is run into a solution of the unsubstituted or substituted anthranilic acid of the formula II in from 5 to 25 moles of an aromatic amine per mole of anthranilic acid, at from 10° to 60° C., after which stirring is continued for 30 minutes at 25° C. (cf. J. Chem. Soc. (C) (1968), 1593). The batch can then be worked up by stirring ice-water into the mixture and filtering off the precipitate which forms. Alternatively, it is possible to carry out the reaction by first taking the carboxylic acid halide and adding the anthranilic acid of the formula II.

Examples of suitable aromatic tertiary amines are pyridine, α, β- and γ-picoline, lutidine, quinoline and acridine.

The benzoxazine derivatives of the formula I may also be obtained by reacting an unsubstituted or substituted anthranilic acid of the formula II

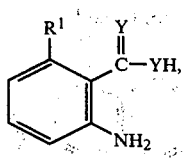

where R¹ and Y have the above meanings, or an alkali metal salt or alkaline earth metal salt of this anthranilic acid, with about the stoichiometric amount of a carboxylic acid halide of the formula III

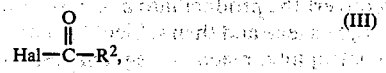

where R² has the meanings given in claim 1 and Hal is halogen, in an inert organic solvent or in water, in the presence or absence of an acid acceptor, at from 0° to 60° C., to give a carboxylic acid amide of the formula IV

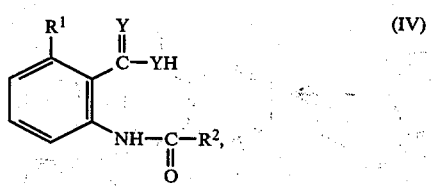

where R¹, R² and Y have the above meanings, and then cyclizing this amide at from 30° to 150° C. in the presence of a dehydrating agent.

If 2,5-dimethylfuran-3-carboxylic acid chloride and anthranilic acid are used as the starting materials, the course of the reaction can be represented by the following equations:

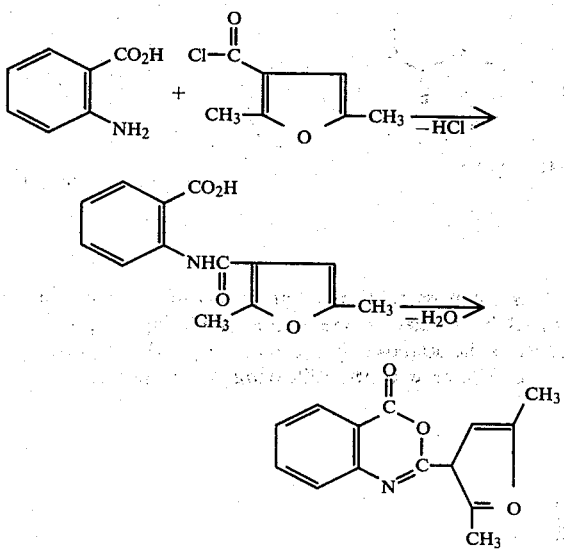

Examples of suitable inert solvents are hydrocarbons, eg. naphtha, gasoline, toluene, pentane, hexane, cyclohexane and petroleum ether, halohydrocarbons, eg. methylene chloride, chloroform, carbon tetrachloride, 1,1- and 1,2-dichloroethane, 1,1,1- and 1,1,2-trichloroethane, chlorobenzene, o-, m- and p-dichlorobenzene and o-, m- and p-chlorotoluene, nitrohydrocarbons, eg. nitrobenzene, nitroethane and o-, m- and p-chloronitrobenzene, nitriles, eg. acetonitrile, butyronitrile and isobutyronitrile, ethers, eg. diethyl ether, di-n-propyl ether, tetrahydrofuran and dioxane, esters, eg. ethyl acetoacetate, ethyl acetate and isobutyl acetate, and amides, eg. formamide, methylformamide and dimethylformamide.

Any of the conventional acid-binding agents may be used as the acid acceptor. Amongst these, alkali metal hydroxides, alkali metal carbonates and tertiary organic bases are preferred. Specific examples of particularly suitable compounds are sodium hydroxide, sodium carbonate, sodium bicarbonate, triethylamine, pyridine, trimethylamine, α-, β- and γ-picoline, lutidine, N,N-dimethylaniline, N,N-dimethylcyclohexylamine, quinoline, tri-n-propylamine and tri-n-butylamine. Advantageously, the acid acceptor is employed in an amount equivalent to the carboxylic acid halide of the formula III.

Suitable dehydrating agents are symmetrical and mixed carboxylic acid anhydrides, eg. acetic anhydride, propionic anhydride, butyric anhydride, formic-acetic anhydride, formic-propionic anhydride and acetic-propionic anhydride, as well as dicyclohexylcarbodiimide and thionyl chloride. The cyclization is carried out with from 1 to 10 moles of dehydrating agent per mole of carboxylic acid amide of the formula IV.

The starting materials of the formulae II and III are employed in about the stoichiometric ratio, ie. to within ±10% of this ratio.

Advantageously, the process is carried out by adding the carboxylic acid halide of the formula III and the equivalent amount of acid acceptor from two separate feeds, at from 0° to 60° C., to an about equivalent amount of the anthranilic acid of the formula II, or a salt thereof, in an inert organic solvent or in water. The mixture is then stirred for 15 minutes at room temperature, after which it is concentrated if necessary, acidified, whilst warm, with 5 N hydrochloric acid, cooled and filtered (J. Org. Chem. 2 (1944), 396), giving a N-acyl-2-aminobenzoic acid. This can be cyclized to the required 4H-3,1-benzoxazine in the presence of a 5- to 10-fold amount of acetic anhydride by stirring under reflux, with or without distillation of the acetic acid formed. To work up the mixture, excess acetic anhydride is removed on a rotary evaporator under reduced pressure and, if necessary, the product is purified by recrystallization. The carboxylic acid halide may also be introduced first into the receiver instead of the anthranilic acid.

Instead of using acetic anhydride, the cyclization can also be carried out with from 1 to 4 moles of dicyclohexylcarbodiimide or thionyl chloride per mole of N-acyl-2-aminobenzoic acid, at 30°–150° C.

In the case of reactive substituents R⁶, for example a carbamic acid ester group, it is advantageous first to prepare a nitro-substituted intermediate and then to react this, after reduction, with an acylating agent, for example as shown in the following equations:

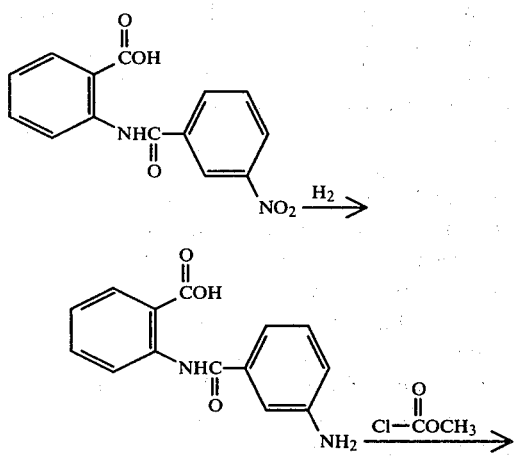
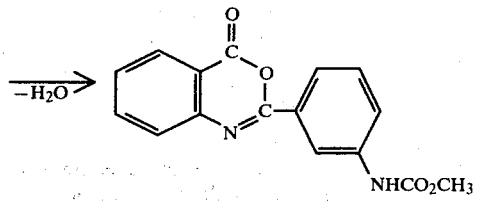

However, it is also possible first to prepare a nitro-substituted 2-phenyl-3,1-benzoxazin-4-one, reduce this, convert the product into a reactive isocyanate by means of phosgene and then subject the latter to reactions with nucleophilic reactants, eg. amines, mercaptans or alcohols.

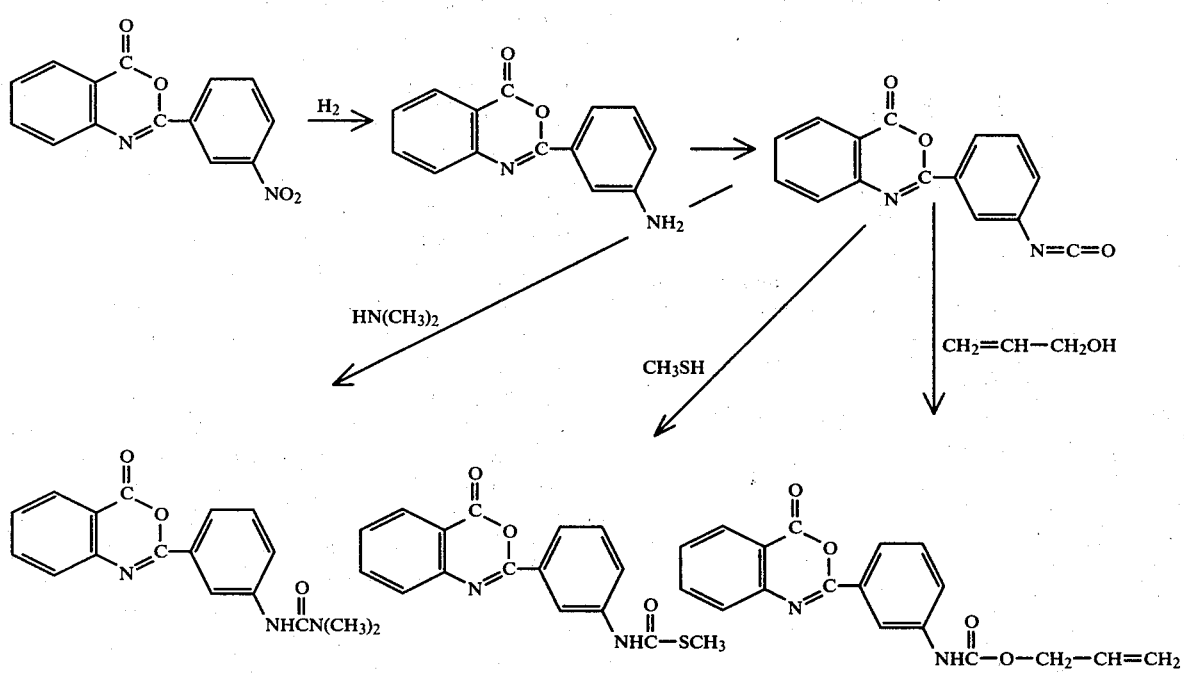

It is also possible to react an amino-substituted 2-phenyl-3,1-benzoxazin-4-one with an acylating reagent, eg. a carboxylic acid or sulfonic acid anhydride or chloride, in accordance with the following equations:

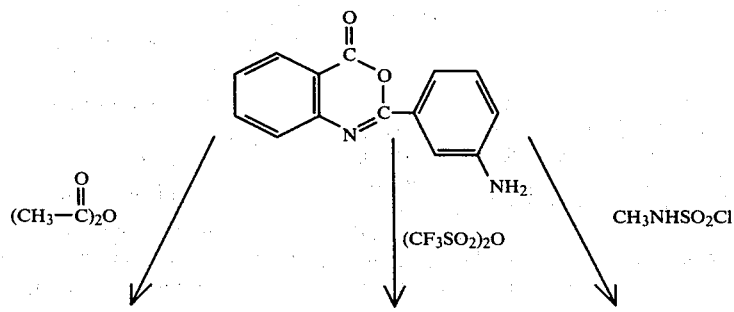

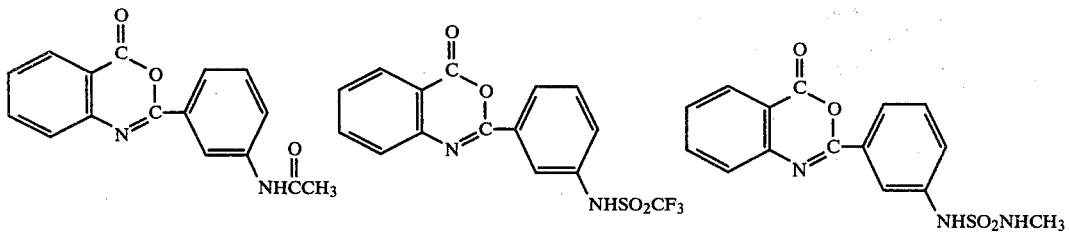

In the case of fluoroalkoxy-substituted or fluoroalkyl-mercapto-substituted 2-phenyl-3,1-benzoxazin-4-ones, it is advantageous to convert a fluoroalkoxy-substituted or fluoroalkylmercapto-substituted benzoic acid, by conventional methods, into the corresponding acid chloride (Houben-Weyl, Methoden der organischen Chemie, 8, 463 et seq., 4th edition, Georg-Thieme-Verlag, Stuttgart, 1952) and then convert the acid chloride, by means of an unsubstituted or substituted anthranilic acid, into the corresponding amide by a conventional method. The amide is then converted to the substituted 2-phenyl-3,1-benzoxazin-4-one by cyclization in the presence of a dehydrating agent.

To isolate the 4H-3,1-benzoxazine derivatives of the formula I from the reaction mixture, the latter may be treated with water, dilute alkali or dilute acid to separate out by-products, such as unconverted anthranilic acid, acid chloride or base hydrochloric, and may then be dried and concentrated. Where necessary, the end products can be purified by recrystallization or chromatography.

The following are examples of the preparation of carboxylic acid halides of the formula III to serve as intermediates for 4H-3,1-benzoxazin-4-ones:

3-Chloro-4-chlorodifluoromethoxybenzoyl fluoride

3-Chloro-4-methoxybenzoic acid is converted by means of thionyl chloride, by a conventional method, to 3-chloro-4-methoxybenzoyl chloride of boiling point 106° C./0.13 mbar and melting point 45°–50° C.

Chlorination of a mixture of 166 parts by weight of 3-chloro-4-methoxybenzoyl chloride and 10 parts by weight of phosphorus pentachloride for 7 hours at 195°–205° C. gives 208 parts by weight of 3-chloro-4-trichloromethoxybenzoyl chloride of boiling point 114° C./0.13 mbar and $n_D^{25} = 1.5780$.

105 Parts by weight of 3-chloro-4-trichloromethoxybenzoyl chloride are introduced over 5 minutes into 92 parts by weight of antimony trifluoride at 90° C., whilst stirring, and the mixture is then stirred for 15 minutes at 110°–120° C. Distillation under reduced pressure gives 39.5 parts by weight of 3-chloro-4-chlorodifluoromethoxybenzoyl fluoride of boiling point 96°–105° C./13 mbar and $n_D^{22} = 1.5185$.

3-Chloro-4-trifluoromethoxybenzoyl fluoride

64 Parts by weight of 3-chloro-4-trichloromethoxybenzoyl chloride are introduced over 6 minutes into a mixture of 1.1 parts by weight of antimony pentachloride and 70 parts by weight of antimony trifluoride at 90° C., whilst stirring. The reaction mixture is stirred for 20 minutes at 190° C. and is then distilled under reduced pressure, giving 25 parts by weight of 3-chloro-4-trifluoromethoxybenzoyl fluoride, of $n_D^{25} = 1.4649$.

3-Chlorodifluoromethoxy-4-chloro-benzoyl fluoride

A mixture of 86 parts by weight of 3-methoxy-4-chlorobenzoyl chloride and 5 parts by weight of phosphorus pentachloride is chlorinated for 7 hours at 195°–205° C., giving 112 parts by weight of 3-trichloromethoxy-4-chlorobenzoyl chloride of boiling point 92°–96° C./0.13 mbar.

69 Parts by weight of 3-trichloromethoxy-4-chlorobenzoyl chloride are introduced over 4 minutes into 60 parts by weight of antimony trifluoride at 90° C., whilst stirring, and the mixture is then stirred for 20 minutes at 110° C. Distillation gives 55 parts by weight of 3-chlorodifluoromethoxy-4-chlorobenzoyl fluoride of boiling point 88°–90° C./13 mbar and $n_D^{22} = 1.5350$.

3-Trifluoromethoxy-4-chlorobenzoyl fluoride 30.8 Parts by weight of 3-trichloromethoxy-4-chlorobenzoyl chloride are introduced over 3 minutes into a mixture of 35.7 parts by weight of antimony trifluoride and 1 part by weight of antimony pentachloride at 90° C., whilst stirring, and the mixture is then stirred for 20 minutes at 190° C. Subsequent distillation gives 19 parts by weight of 3-trifluoromethoxy-4-chloro-benzoyl fluoride of boiling point 96°–103° C./39 mbar.

3-(1',1',2'-Trifluoro-2'-chloroethoxy)-benzoyl chloride 52.4 Parts by weight of chlorotrifluoroethylene are introduced, over 10 hours, into a mixture of 46.5 parts by weight of methyl 3-hydroxybenzoate and 9.5 parts by weight of potassium hydroxide powder in 50 parts by weight of acetone, refluxing at 45°–52° C. After concentrating the reaction mixture on a rotary evaporator under reduced pressure, the residue is taken up in methylene chloride and the solution is extracted with sodium bicarbonate solution, dried and evaporated, giving 69.5 parts by weight of methyl 3-(1',1',2'-trifluoro-2'-chloroethoxy)-benzoate of $n_D^{25} = 1.4710$.

40 Parts by weight of methyl 3-(1',1',2'-trifluoro-2'-chloroethoxy)-benzoate, in a mixture of 8.4 parts by weight of potassium hydroxide, 100 parts by weight of water and 5 parts by weight of tetrahydrofuran, are stirred for 15 minutes at 95° C. The resulting solution is acidified with concentrated hydrochloric acid and the precipitate formed is filtered off and dried; 35 parts of 3-(1',1',2'-trifluoro-2'-chloroethoxy)benzoic acid of melting point 79°–85° C. are obtained.

35 Parts by weight of 3-(1',1',2'-trifluoro-2'-chloroethoxy)-benzoic acid are converted to 3-(1',1',2'-trifluoro-2'-chloroethoxy)-benzoyl chloride, of $n_D^{22} = 1.4900$ (IR: C=O 1,760 and 1,742 cm$^{-1}$) in a conventional manner by means of 20.2 parts by weight of thionyl chloride and 0.2 part by weight of pyridine as the catalyst. Yield: 34.5 parts by weight, corresponding to 92% of theory.

3,4-Difluorobenzoyl chloride

36 Parts by weight of 3,4-difluorobenzoic acid (J. org. Chem. 27 (1962), 2,923) are converted to the corresponding acid chloride, of boiling point 63°–66° C./10 mbar (IR: C=O 1,752 cm$^{-1}$) in a conventional manner by means of 59.5 parts by weight of thionyl chloride and 0.2 part by weight of pyridine. Yield: 25 parts by weight of 3,4-difluorobenzoyl chloride.

3-Chloro-4-fluorobenzoyl chloride

100 Parts by weight of 3-chloro-4-fluorobenzoic acid (J. Chem. Soc. 1693, 2784) are converted to the corresponding acid chloride in a conventional manner by means of 83.3 parts by weight of thionyl chloride and 0.2 part by weight of pyridine. Yield: 63.1 parts by weight of 3-chloro-4-fluorobenzoyl chloride, of boiling point 45°–47° C./0.13 mbar.

The Examples which follow illustrate the preparation of some 4H-3,1-benzoxazine derivatives. Parts by weight bear the same relation to parts by volume as that of the kilogram to the liter.

EXAMPLE 1

Preparation of 2-(m-methoxycarbamylphenyl)-3,1-benzoxazin-4-one

3-Nitrobenzoyl chloride and anthranilic acid are converted by a conventional method to 3-nitrobenzoylanthranilic acid, of melting point 242°–247° C. (J. Am. Chem. Soc. 33 (1911), 952).

56 parts by weight of the amide thus obtained, in a mixture of 400 parts by volume of absolute ethanol and 15 parts by weight of Raney nickel, are hydrogenated for 3 hours at 60° C. under a pressure of 100 bar. The reaction mixture is filtered, the filter residue is washed with ethanol, and the filtrates are concentrated under reduced pressure. The residue obtained is taken up in 3 N sodium hydroxide solution and the resulting solution is extracted once with ether and stirred into dilute hydrochloric acid. After filtering off the product, and drying it, 3-aminobenzoylanthranilic acid (melting point 260° C., with decomposition) is obtained.

41 parts by weight of the acid thus obtained and 17.1 parts by weight of triethylamine are dissolved in 700 parts by volume of 1,2-dichloroethane and 16.1 parts by weight of methyl chloroformate are added from a dropping funnel, at 25° C., whilst stirring. After stirring the mixture for 12 hours, the precipitate which has formed is filtered off, washed with water and dried, giving m-methoxycarbamyl-benzoylanthranilic acid of melting point 216°–220° C.

16 parts by weight of the compound thus obtained and 130 parts by volume of acetic anhydride are refluxed for 1 hour, whilst stirring. When the mixture has cooled, the precipitate is filtered off, washed with ether and dried, giving 13 parts by weight of 2-(m-methoxycarbamylphenyl)-3,1-benzoxazin-4-one of melting point 223°–226° C.; yield: 88% of theory.

EXAMPLE 2

Preparation of 2-(m-ethoxycarbamylphenyl)-3,1-benzoxazin-4-one

21 Parts by weight of 2-(m-nitrophenyl)-3,1-benzoxazin-4-one, in a mixture of 160 parts by volume of 1,4-dioxane and 2.5 parts by weight of 5% strength palladium on charcoal, are hydrogenated for 10 hours at 50° C. under a pressure of 20 bar. The catalyst is removed by filtration and the reaction mixture is concentrated under reduced pressure and then stirred with 50 parts by volume of 1 N sodium hydroxide solution, and the precipitated 2-(m-aminophenyl)-3,1-benzoxazin-4-one is washed with water and dried; melting point 150°–154° C.

40 Parts by weight of 2-(m-aminophenyl)-3,1-benzoxazin-4-one are suspended in 300 parts by volume of chlorobenzene and the suspension is treated with hydrogen chloride gas until saturated therewith, and then with phosgene gas for 4 hours at 110° C. The clear solution is concentrated under reduced pressure and the residue is then washed with ether and petroleum ether, giving 39 parts by weight of 2-(m-isocyanatophenyl)-3,1-benzoxazin-4-one of melting point 115°–121° C.

2.4 parts by weight of absolute ethanol and 1 drop of triethylamine as the catalyst are added to a solution of 13.2 parts by weight of 2-(m-isocyanatophenyl)-3,1-benzoxazin-4-one in 150 parts by volume of 1,2-dichloroethane at 25° C., whilst stirring. The reaction mixture is stirred for 2 hours at 50° C. and cooled, and the product is filtered off. After washing the latter with ether and petroleum ether, 2-(m-ethoxycarbamyl-phenyl)-3,1-benzoxazin-4-one is obtained in the form of colorless crystals of melting point 179°–183° C. Yield: 10.5 parts by weight, corresponding to 68% of theory.

EXAMPLE 3

Preparation of 2-(m-1',1',2',2'-tetrafluoroethoxyphenyl)-3,1-benzoxazin-4-one 39.4 parts by weight of thionyl chloride are added to a suspension of 65 parts by weight of m-(1,1,2,2-tetrafluoroethoxy)-benzoic acid in 500 parts by volume of 1,2-dichloroethane and the mixture is stirred for 3 hours under reflux. It is then concentrated under reduced pressure, and after filtering off a small amount of starting material which has precipitated, m-(1,1,2,2-tetrafluoroethoxy)-benzoyl chloride is obtained as a yellowish oil. The IR spectrum shows C=O bands at 1,770 and 1,748 cm$^{-1}$ and fluoroalkoxy bands at 1,225, 1,190 and 1,125 cm$^{-1}$.

25.7 Parts by weight of m-(1,1,2,2-tetrafluoroethoxy)-benzoyl chloride and 10.1 parts by weight of triethylamine are added from two separate feeds, over 15 minutes, to a stirred mixture of 13.7 parts by weight of anthranilic acid and 300 parts by volume of 1,2-dichloroethane, and stirring is continued for 12 hours at room temperature. The reaction mixture is extracted with 0.5 N hydrochloric acid and with water, dried over magnesium sulfate and concentrated under reduced pressure. After triturating the product in 0.5 N hydrochloric acid, filtering off and washing with water, m-(1,1,2,2-tetrafluoroethoxy)-benzoylanthranilic acid of melting point 159°–163° C. is obtained.

21 parts by weight of the product thus obtained are cyclized for 3 hours in 200 parts by volume of refluxing acetic anhydride, whilst stirring. The reaction mixture is then concentrated under reduced pressure, the residue is taken up in methylene chloride and the solution is chromatographed over neutral aluminum oxide. After concentrating the eluate, 16 parts by weight of 2-(m-1',1',2',2'-tetrafluoroethoxyphenyl)-3,1-benzoxazin-4-one of melting point 95°–98° C. are obtained.

EXAMPLE 4

Preparation of
2-(m-difluoromethoxy-phenyl)-3,1-benzoxazin-4-one

260 Parts by weight of chlorodifluoromethane are passed, over 1.5 hours, into a stirred mixture of 221 parts by weight of m-cresol, 412 parts by weight of sodium hydroxide, 600 parts by volume of 1,4-dioxane and 500 parts by volume of water, at 67°-70° C. After stirring for 45 minutes at 68° C., the reaction mixture is cooled, diluted with 1,000 parts by volume of water and extracted four times with 200 parts by volume of ether. After drying the ether phase, concentrating under reduced pressure and distilling, 172 parts by weight of m-tolyl difluoromethyl ether of boiling point 64°-67° C./24.7 mbar are obtained.

A mixture of 47.4 parts by weight of m-tolyl difluoromethyl ether, 77 parts by weight of magnesium sulfate, 134.3 parts by weight of potassium permanganate and 1,900 parts by volume of water is stirred for 3 hours at 50°-60° C. for 2 hours at 90° C. After destroying excess permanganate with ethanol, the solution is filtered whilst still hot and the filtrate is then acidified. The precipitate formed is taken up in methylene chloride and the extract is dried; after concentrating under reduced pressure, 3-difluoromethoxybenzoic acid of melting point 85°-87° C. is obtained.

The above acid can be converted by means of thionyl chloride, in a conventional manner, to 3-difluoromethoxybenzoyl chloride of $n_D^{25} = 1.5083$.

25 parts by weight of 3-difluoromethoxybenzoyl chloride and 12.2 parts by weight of triethylamine are added over 15 minutes, from 2 separate feeds, to a stirred mixture of 16.6 parts by weight of anthranilic acid in 360 parts by weight of 1,2-dichloroethane at 25°-30° C. After stirring for 2 hours at 25° C., the reaction mixture is extracted with 0.5 N hydrochloric acid and with water. The organic phase is then extracted with four times 100 parts of 0.5 N sodium hydroxide solution, and the extracts are stirred into dilute hydrochloric acid. After filtration and drying, 30.4 parts by weight, corresponding to 82% of theory, of N-(3-difluoromethoxybenzoyl)-anthranilic acid of melting point 186°-191° C. are obtained. 8.33 Parts by weight of thionyl chloride are introduced into a stirred mixture of 18 parts by weight of N-(3-difluoromethoxybenzoyl)-anthranilic acid in 250 parts by weight of 1,2-dichloroethane at 25° C.; the mixture is then stirred for 4 hours under reflux. When it has cooled, the reaction mixture is extracted with 100 parts by volume of ice-water and 100 parts by volume of 0.5 N sodium hydroxide solution and is chromatographed over neutral aluminum oxide. 12 parts by weight, corresponding to 71% of theory, of 2-(3'-difluoromethoxy-phenyl)-3,1-benzoxazin-4-one, of melting point 84°-87° C., are obtained.

EXAMPLE 5

Preparation of
2-(m-trifluoromethylsulfinyl-phenyl)-3,1-benzoxazin-4-one 8.85 Parts by weight of m-chloroperbenzoic acid in 150 parts of methylene chloride are added to a mixture of 16.2 parts of 2-(m-trifluoromethylmercapto-phenyl)-3,1-benzoxazin-4-one and 130 parts of methylene chloride at room temperature. The mixture is then stirred for a further 22 hours. The precipitate, which has formed is dissolved by adding 100 parts of methylene chloride and the solution obtained is extracted twice with 0.3 N sodium hydroxide solution and with water. It is then dried over magnesium sulfate and chromatographed over aluminum oxide, giving 12.4 parts of 2-(m-trifluoromethylsulfinyl-phenyl)-3,1-benzoxazin-4-one, of melting point 106°-108° C.

EXAMPLE 6

Preparation of
2-(m-trifluoromethylsulfonyl-phenyl)-3,1-benzoxazin-4-one

Following the method described in Example 5, but starting from 17.3 parts of m-chloroperbenzoic acid, 12 parts of 2-(m-trifluoromethylsulfonyl-phenyl)-3,1-benzoxazin-4-one, of melting point 96°-102° C., are obtained.

Using corresponding methods, the following 4H-3,1-benzoxazine derivatives of the formula I can be prepared:

| $R^2$ | Y | m.p. [°C.] | $R^2$ | Y | m.p. [°C.] |
| --- | --- | --- | --- | --- | --- |
| –⟨⟩–SCH₃ | O | | | | |
| –⟨⟩(SCH₃) | O | 120–123 | –⟨⟩(OCHF₂) | S | |
| –⟨⟩–SC₂H₅ | S | | –⟨⟩–OCCl₃ | O | 145–149 |
| –⟨⟩(SC₂H₅) | O | | –⟨⟩(OCCl₃) | O | 107–110 |
| –⟨⟩–OCF₃ | O | 87–90 | –⟨⟩–OCF₂CF₃ | O | |

-continued

| R² | Y | m.p. [°C] | R² | Y | m.p. [°C] |
|---|---|---|---|---|---|
| -C6H4-OCF3 (3-) | O | 94–95 | -C6H4-OCF2CF3 (4-) | O | 108–112 |
| -C6H4-OCF2CF2H (4-) | O | 98–102 | -C6H4-O-CH(CF3)2 (4-) | S | |
| -C6H4-OCF2Cl (4-) | O | | -C6H4-O-CH(CF3)2 (3-) | O | |
| -C6H4-OCF2Cl (3-) | O | 82–86 | -C6H4-SCF2H (4-) | O | |
| -C6H4-OCHF2 (4-) | O | | -C6H4-SCF3 (3-) | O | 87–90 |
| -C6H4-OCF3 (3-) | S | | -C6H3(CH3)-SCF3 | S | |
| -C6H4-SOCH3 (4-) | O | | -C6H4-SO2CF2H (4-) | O | |
| -C6H4-SOCH3 (3-) | O | 146–151 | -C6H4-SO2CF2H (3-) | O | |
| -C6H4-SOCH3 (3-) | S | | -C6H4-SO2CF2H (4-) | S | |
| -C6H4-SOC2H5 (4-) | S | | -C6H4-SO2CF3 (4-) | O | |
| -C6H4-SOC2H5 (3-) | S | | -C6H4-SO2CF2Cl (3-) | O | |
| -C6H4-SOCF2Cl (3-) | O | | -C6H4-SO2CF3 (3-) | S | |
| -C6H4-SO2CH3 (4-) | O | | -C6H4-SO2CF2CF3 (4-) | O | |
| -C6H4-SO2CH3 (3-) | O | 200–202 | -C6H4-SO2CF2CF3 (3-) | O | |
| -C6H4-SO2C2H5 (4-) | O | | -C6H4-N(CF3)(SCF3) (4-) | O | |
| -C6H4-SO2C2H5 (3-) | O | | -C6H4-N(CF3)(SCF3) (3-) | O | |
| -C6H4-SO2CH2Cl (4-) | O | | -C6H4-C(O)-OCH3 (4-) | O | |

| Y | R² | m.p. [°C] |
|---|---|---|

4,315,766

-continued

| | | |
|---|---|---|
| O | –C₆H₅-SCCl₃ | 130–134 |
| O | –C₆H₅-SCF₂Cl | |
| S | –C₆H₃(CH₃)(NO₂) (2-CH₃, 3-NO₂) | |
| O | –C₆H₃(CH₃)(NO₂) (2-CH₃, 3-NO₂) | 170–173 |
| O | –C₆H₃(NO₂)(OCF₃) (2-NO₂, 3-OCF₃) | |
| O | –C₆H₃(CH₃)(OCHF₂) (2-CH₃, 3-OCHF₂) | |
| O | –C₆H₃(OCHF₂)(CH₃) (2-OCHF₂, 3-CH₃) | |
| O | –C₆H₃(NO₂)(CH₃) (2-NO₂, 3-CH₃) | 155–158 |
| O | –C₆H₃(NO₂)(Cl) (2-NO₂, 3-Cl) | |
| O | –C₆H₃(Cl)(NO₂) (2-Cl, 3-NO₂) | 177–180 |
| O | –C₆H₃(SCF₃)(Cl) (2-SCF₃, 3-Cl) | |
| O | –C₆H₃(Cl)(SCF₃) (2-Cl, 3-SCF₃) | |
| O | –C₆H₃(F)(SCF₃) (2-F, 3-SCF₃) | |
| O | –C₆H₃(F)(F) (2-F, 3-F) | 149–153 |
| O | –C₆H₃(Cl)(F) (2-Cl, 3-F) | |
| O | –C₆H₃(F)(Cl) (2-F, 3-Cl) | 188–191 |
| O | –C₆H₃(Br)(F) (2-Br, 3-F) | |

-continued
| | | | |
|---|---|---|---|
| S | 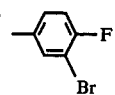 | | |
| O | 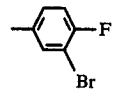 | | |
| O | 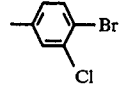 | | |
| O | 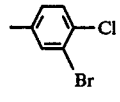 | | |
| O | 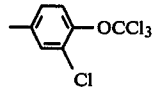 | 174–178 | |
| O | 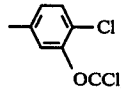 | 147–150 | |
| O | 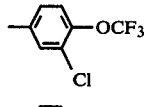 | 117–120 | |
| O | 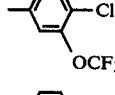 | 152–155 | |
| O | 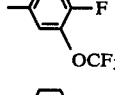 | | |
| O | 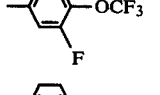 | | |
| O | 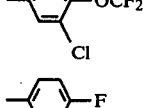 | 103–106 | |
| O | 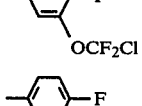 | | |
| O | 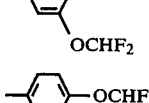 | | |
| O | 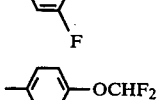 | | |
| O | 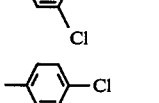 | | |
| O | 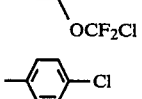 | 108–111 | |
| O | 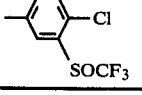 | | |

-continued

| O | R² | m.p. [°C] |
|---|---|---|
| O | 4-methyl-2-Cl-phenyl with SO₂CF₃ | |
| S | 4-methyl-2-Cl-phenyl with SO₂CH₃ | |
| O | 4-methyl-2-CH₃-phenyl with SO₂CH₃ | |
| O | 4-methyl-2-NO₂-phenyl with CO₂CH₃ | |
| O | 3-methyl-5-NO₂-phenyl with CO₂CH₃ | 157–160 |
| S | 4-methyl-2-Cl-phenyl with CO₂CH₃ | |

| R² | Y | m.p. [°C] | R² | Y | m.p. [°C] |
|---|---|---|---|---|---|
| —C₆H₄—SO₂CH₂Cl | O | | | | |
| —C₆H₄—OCF₂CHFCl | O | 105–108 | —C₆H₄—NHC(O)N(CH₃)₂ | O | |
| —C₆H₄—C(O)OCH₃ | S | | —C₆H₄—NHC(O)NHCH₃ | O | |
| —C₆H₄—C(O)OC₂H₅ | O | | —C₆H₄—OCF₂CHFCl | O | |
| —C₆H₄—C(O)OCH₃ | O | | —C₆H₄—NH—C(O)—NHCH₃ | O | |
| —C₆H₄—C(O)OC₂H₅ | O | | —C₆H₄—NH—C(O)—NHCH₃ | S | |
| —C₆H₄—C(O)O—i-C₃H₇ | O | | —C₆H₄—NH—C(O)—N(CH₃)(OCH₃) | O | |
| —C₆H₄—C(O)O—i-C₃H₇ | O | | —C₆H₄—NH—C(O)—N(CH₃)(OCH₃) | O | |
| —C₆H₄—C(O)O—CH₂—CH=CH₂ | O | | —C₆H₄—NH—C(O)H | O | |

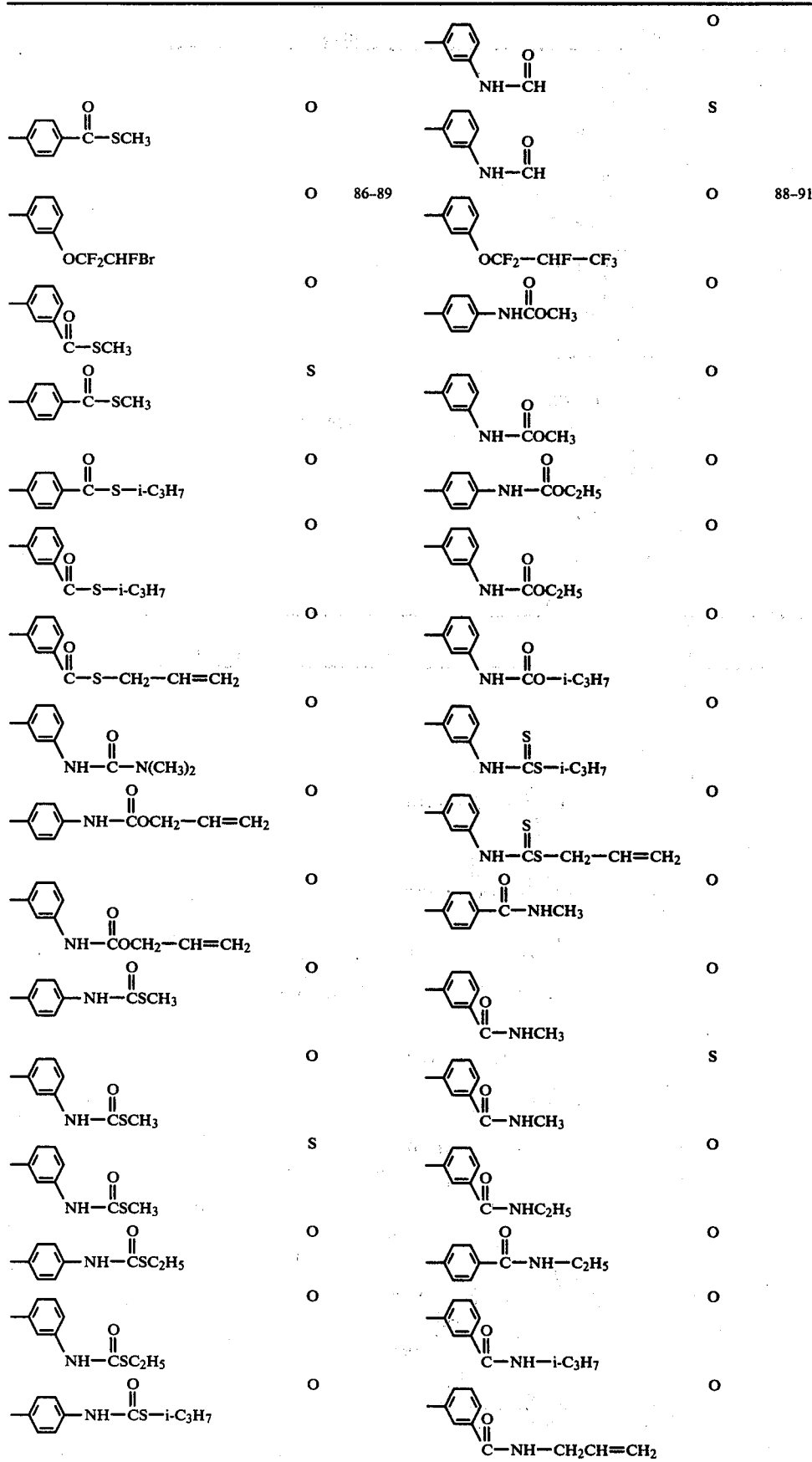

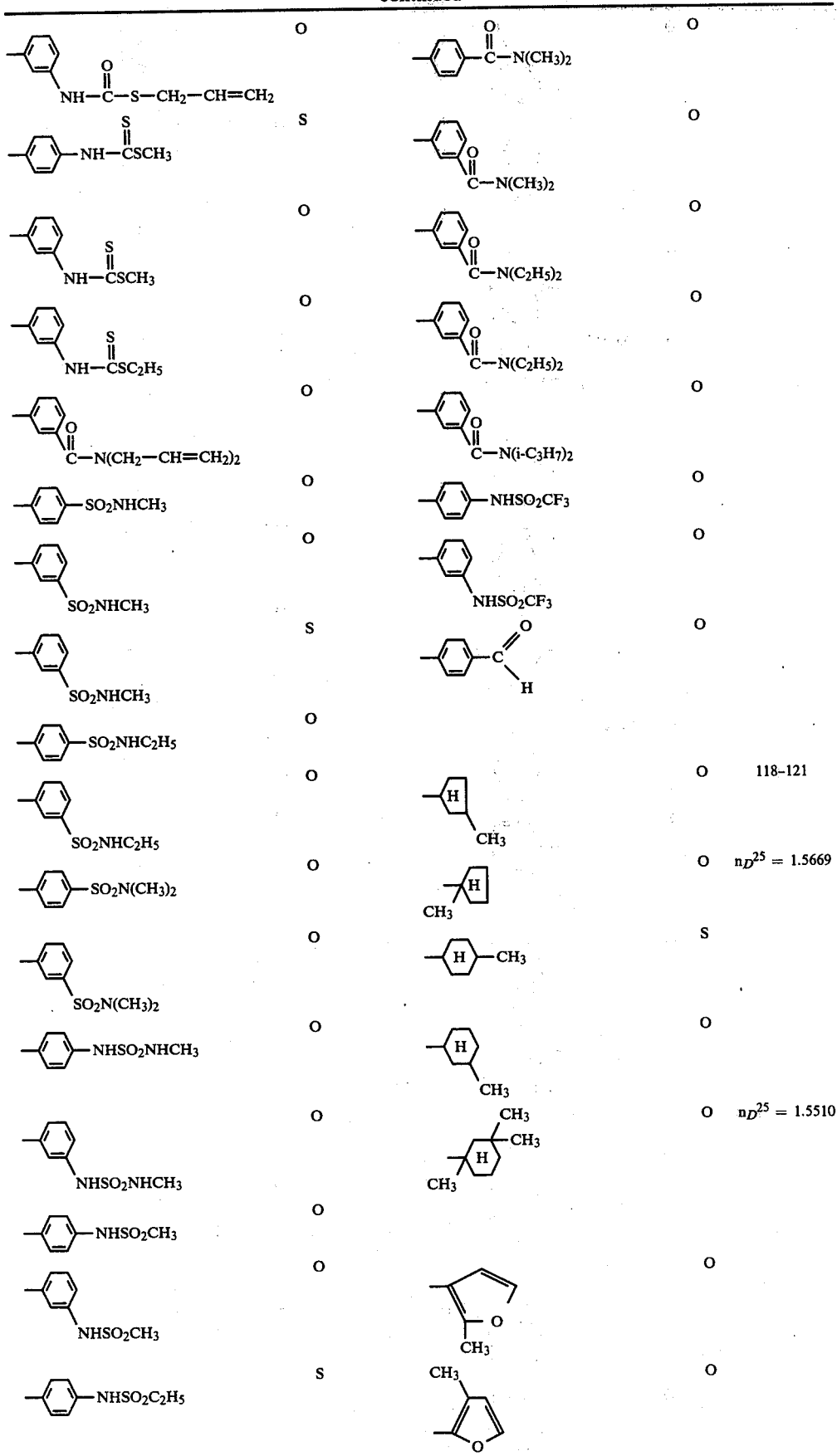

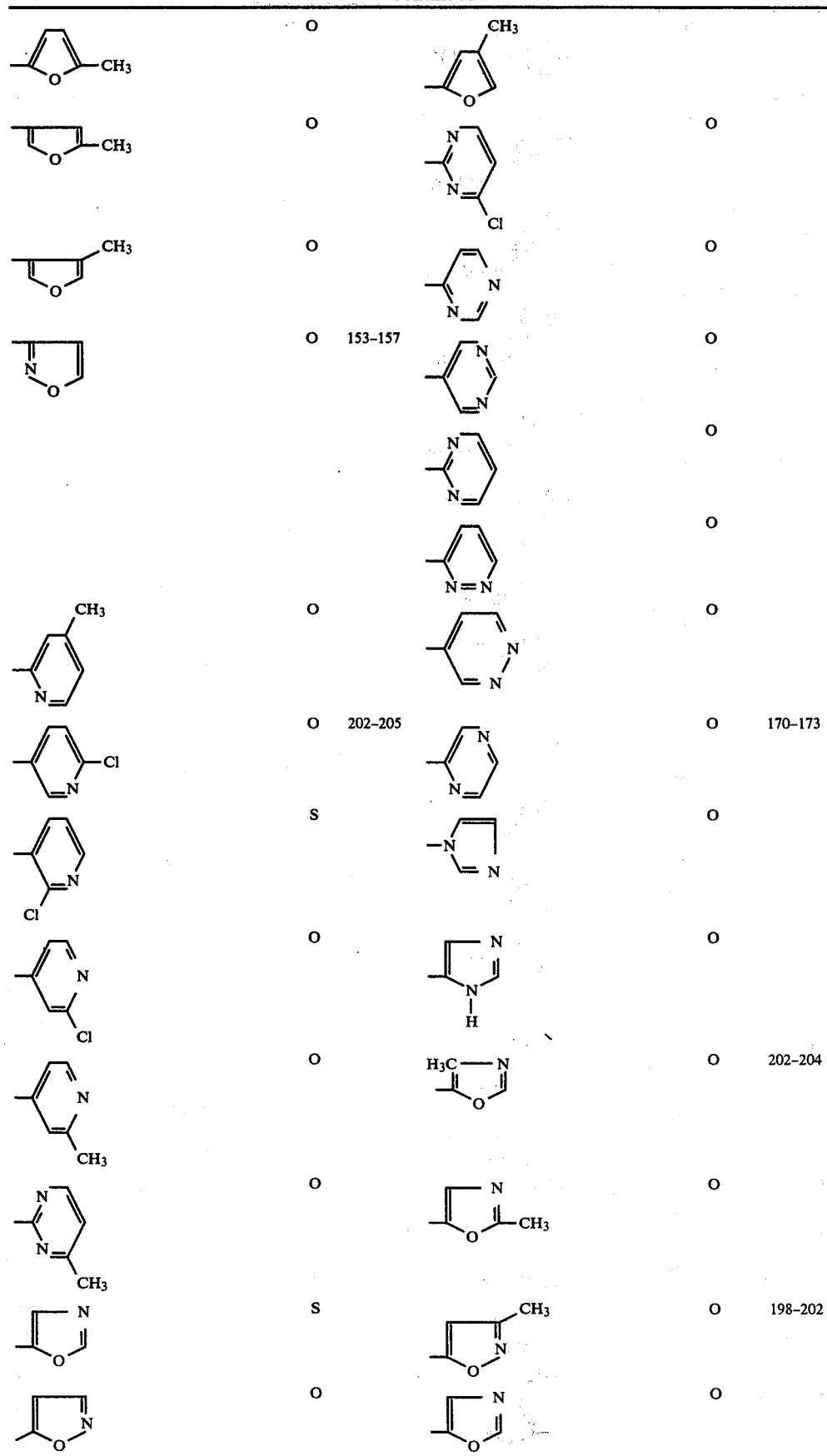

-continued
| | | | | |
|---|---|---|---|---|
| (oxazole) | O | (norbornyl) | O | 93–96 |
| 2,5-dimethylfuran | O 114–116 | (triazine) | O | |
| (triazine-CH3) | O | (N-methyl triazole) | O | |
| 2-methylmorpholinyl-N— | O 103–105 | 2,6-dimethylmorpholinyl-N— | O | 114–117 |
| —CH2—C6H4—CF3 (m) | O 79–81 | | | |
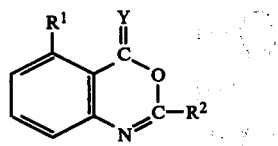
| R¹ | Y | R² | m.p. [°C] |
|---|---|---|---|
| Br | O | C6H5 | |
| SCN | O | C6H5 | |
| CN | O | C6H5 | |
| Cl | O | C6H5 | 153–155 |
| Cl | S | C6H5 | |
| F | O | C6H5 | 157–161 |
| CCl3 | O | C6H5 | |
| CF3 | O | C6H5 | |
| CF3 | S | C6H5 | |
| Cl | O | —C6H4—SCF3 (m) | 124–128 |
| C(=O)—N(CH3)2 | O | C6H5 | |
| OCH3 | O | C6H5 | |
| SCH3 | O | C6H5 | |
| SOCH3 | O | C6H5 | |
| SO2CH3 | O | C6H5 | |
| NO2 | O | C6H5 | 180 |
| SO2OCH3 | O | C6H5 | |
| CH3 | O | —C6H4—OCF3 (p) | 125–127 |
| SCN | O | —C6H4—OCF3 (m) | |
| Cl | O | —C6H4—OCF3 (p) | 137–138 |
| SO2N(CH3)2 | O | —C6H4—OCF3 (m) | |
| CH3 | O | C6H5 | 152–155 |
| F | O | —C6H4—OCF2CF2H (p) | 98–100 |

-continued

| R¹ | Y | R² | m.p. [°C] |
|---|---|---|---|
| F | O | 3-(OCF₂CF₂H)-phenyl | 92–96 |
| CO₂CH₃ | O | C₆H₅ | |
| Cl | S | 3-(OCF₃)-phenyl | |
| Cl | O | 3-(OCF₃)-phenyl | 140–143 |

| R¹ | O | R² | m.p. [°C] |
|---|---|---|---|
| Cl | O | 4-Cl-3-F-phenyl | |
| F | O | 4-F-3-Cl-phenyl | 205–208 |
| Cl | O | 4-Cl-3-(SCF₃)-phenyl | |
| Cl | O | 4-F-3-(SCF₃)-phenyl | |
| Cl | O | 4-Cl-3-(OCCl₃)-phenyl | |

| R¹ | Y | R² | m.p. [°C] |
|---|---|---|---|
| Cl | O | 4-Cl-3-(OCF₃)-phenyl | |
| F | O | 4-Cl-3-(OCHF₂)-phenyl | |
| Cl | O | 4-Cl-3-(OCF₂Cl)-phenyl | |
| F | O | 4-Cl-3-(OCF₃)-phenyl | |
| CH₃ | O | 4-Cl-3-(OCF₃)-phenyl | |
| CH₃ | O | 4-Cl-3-(OCHF₂)-phenyl | |
| CH₃ | O | 4-Cl-3-(SO₂CF₃)-phenyl | |

-continued
| | | | |
|---|---|---|---|
| CH₃ | O | 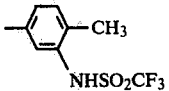 2-methyl, NHSO₂CF₃ | |
| CH₃ | O | 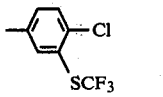 Cl, SCF₃ | |
| CH₃ | O | 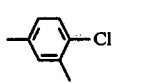 Cl, F | |
| CH₃ | O | 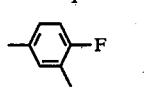 F, Cl | |
| CN | O | 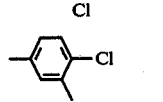 Cl, OCF₃ | |
| CN | O | 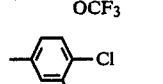 Cl, F | |
| F | O | 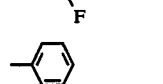 OCF₃ | 93–97 |
| Cl | O | 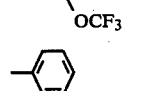 OCF₂CF₂H | 125–129 |
| F | O | 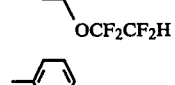 OCHF₂ | 102–104 |
| Cl | O | 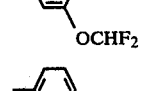 OCHF₃ | 112–116 |
| Cl | O | 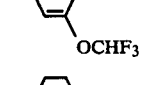 OCF₂Cl | 115–116 |
| NO₂ | O | 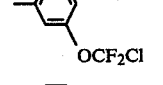 CF₃ | 154–152 |
| Cl | O | 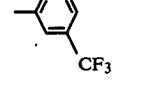 F, Cl | 168–171 |
| Cl | O | 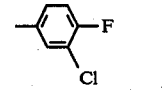 SCF₂Cl | |
| CN | O | 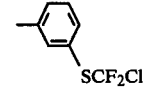 F, Cl | |
| CN | O | 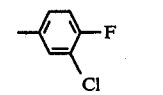 Cl, SCF₃ | |
| CN | O | 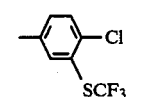 Cl, CF₃ | |

| | -continued |
|---|---|
| NO₂ | O—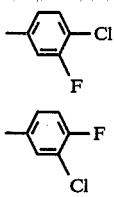 |
| NO₂ | O—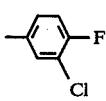 |

The active ingredients according to the invention may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure as fine a distribution of the active ingredient as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethylsulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

Examples of formulations are as follows.

I. 90 Parts by weight of the compound of Example 1 is mixed with 10 parts by weight of N-methyl-α-pyrrolidone. A mixture is obtained which is suitable for application in the form of very fine drops.

II. 20 Parts by weight of the compound of Example 2 is dissolved in a mixture consisting of 80 parts by weight of xylene, 10 parts by weight of the adduct of 8 to 10 moles of ethylene oxide with 1 mole of oleic acid-N-monoethanolamide, 5 parts by weight of the calcium salt of dodecylbenzenesulfonic acid, and 5 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

III. 20 Parts by weight of the compound of Example 3 is dissolved in a mixture consisting of 40 parts by weight of cyclohexanone, 30 parts by weight of isobutanol, 20 parts by weight of the adduct of 7 moles of ethylene oxide with 1 mole of isooctylphenol, and 10 parts by weight of the adduct of 40 moles of ethylene oxide with 1 mole of castor oil. By pouring the solution into 100,000 parts by weight of water and finely distributing it therein, an aqueous dispersion is obtained containing 0.02% by weight of the active ingredient.

IV. 20 Parts by weight of the compound of Example 4 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient V. 20 Parts by weight of the compound of Example 2 is well mixed with 3 parts by weight of the sodium salt of diisobutylnaphthalene-α-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 Parts by weight of the compond of Example 1 is intimately mixed with 97 parts by weight of particulate kaolin. A dust is obtained containing 3% by weight of the active ingredient.

VII. 30 Parts by weight of the compound of Example 2 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 Parts of the compound of Example 3 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The influence of various representatives of 4H-3,1-benzoxazine derivatives of the formula I on the growth of unwanted plants is demonstrated in greenhouse experiments.

The vessels employed were plastic flowerpots having a volume of 300 cm$^3$, and which were filled with a sandy loam containing about 1.5% humus. The seeds of the test plants (cf. Table 1) were sown shallow, and separately, according to species, or pregerminated young plants or cuttings were transplanted. Generally, the plants were grown to a height of 3 to 10 cm, depending on the growth shape, before being treated. The compounds were emulsified or suspended in water as vehicle, and sprayed through finely distributing nozzles onto the shoot parts of the plants and the soil not completely covered by plants. The pots were set up in the greenhouse—species from warmer areas at from 20° to 30° C., and species from moderate climates at 10° to 20° C. The experiments were run for from 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The plant species used in the experiments are listed in Table 1.

The results given in the tables below show that the 4H-3,1-benzoxazine derivatives of the formula I have a better herbicidal action than prior art herbicidal benzoxazines, and are well tolerated by a number of crop plants. The compounds according to the invention are predominantly applied after emergence of the unwanted plants, either on cropland or uncropped land.

If the crop plants tolerate the active ingredients less well, application techniques may be used in which the agents are sprayed from suitable equipment in such a manner that the leaves of sensitive crop plants are if possible not touched, and the agents reach the soil or the unwanted plants growing beneath the crop plants (post-directed, lay-by treatment).

TABLE 1

List of plant names

| Botanical name | Abbreviation in tables | Common name |
| --- | --- | --- |
| Acanthospermum hispidum | Acanthosp. hisp. | bristly starbur |
| Arachis hypogaea | | peanuts (groundnuts) |
| Avena sativa | | oats |
| Beta vulgaris | Beta vulg. | sugarbeets |
| Centaurea spp. | | knapweed |
| Chenopodium album | Chenopod. album | lambsquarters (goosefoot) |
| Chrysanthemum segetum | Chrysanth. segetum | corn marigold |
| Cyperus spp. | | nutsedge |
| Datura stramonium | Datura stram. | Jimsonweed |
| Desmodium tortuosum | Desmod. tort. | Florida beggarweed |
| Euphorbia geniculata | Euphorb. genic. | wild poinsettia |
| Glycine max | | soybeans |
| Galeopsis spp. | | hemp-nettle |
| Gossypium hirsutum | Gossyp. hirs. | cotton |
| Hordeum vulgare | | barley |
| Matricaria spp. | Matric. spp. | chamomile |
| Malva neglecta | | common mallow |
| Mercurialis annua | Mercurial. annua | annual mercury |
| Oryza sativa | | rice |
| Sesbania exaltata | | hemp sesbania (coffeeweed) |
| Solanum nigrum | Solan. nigr. | black nightshade |
| Sorghum bicolor | | sorghum |
| Triticum aestivum | | wheat |
| Xanthium pensylvanicum | Xanthium pens. | common cocklebur |
| Zea mays | | Indian corn |

TABLE 2

Selective herbicidal action of new compounds; postemergence treatment in the greenhouse

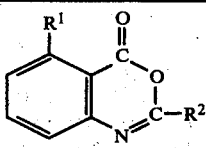

| R¹ | R² | Crop plants - damage in % at appln. rate of 1.0 kg/ha | | | | | Index of herbicidal action at appln. rate of 0.5 kg/ha[x] |
|---|---|---|---|---|---|---|---|
| | | Hordeum vulgare | Oryzn sativa | Sorghum bicolor | Triticum aestivum | Zea mays | |
| H | —⌬—OCF₂CF₂H | 0 | 2 | 0 | 10 | 17 | 87 |
| H | —⌬—OCF₃ | 0 | 0 | 0 | 0 | 9 | 90 |
| H | —⌬—CF₃ (prior art) | 0 | 5 | 30 | 23 | 18 | 58 |

0 = no damage
100 = plants destroyed
[x]calculated from average values obtained with the following plants:
Chenopodium album, Cyperus spp., Chrysanthemum segetum, Datura stramonium, Matricaria spp., Mercurialis annua, Sesbania exaltata and Solanum nigrum

TABLE 3

Selective control of weeds in groundnuts and other crops; postemergence treatment in the greenhouse

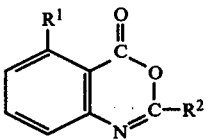

| R¹ | R² | Appln. rate [kg/ha] | Test plants and % damage | | | | | | |
|---|---|---|---|---|---|---|---|---|---|
| | | | Arachis hypogaea | Glycine max | Oryza sativa | Sorghum bicolor | Zea mays | Sesbania exaltata | Xanthium pensylvanicum |
| Cl | —⌬ | 1.0 | 0 | 0 | 5 | 0 | 0 | 82 | 100 |
| H | —⌬ (prior art) | 1.0 | 0 | 7 | 6 | 0 | 6 | 81 | 30 |

0 = no damage
100 = plants destroyed

TABLE 4

Selective control of important broadleaved weeds in soybeans; postemergence treatment in the greenhouse

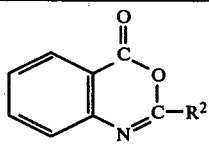

| R² | Appln. rate [kg/ha] | Test plants and % damage | | | | | |
|---|---|---|---|---|---|---|---|
| | | Glycine max | Chenopod. album | Datura stram. | Euphorbia geniculata | Solanum nigrum | Xanthium pens. |
| —⌬—SCF₃ | 0.5 | 12 | 99 | 100 | 92 | 100 | 100 |

TABLE 4-continued

Selective control of important broadleaved weeds in soybeans; postemergence treatment in the greenhouse Structure: 4H-3,1-benzoxazine with C=O, O, N=C-R²

| R² | Appln. rate [kg/ha] | Glycine max | Chenopod. album | Datura stram. | Euphorbia geniculata | Solanum nigrum | Xanthium pens. |
|---|---|---|---|---|---|---|---|
| –(phenyl)–OCF₂Cl (meta) | 0.5 | 8 | 70 | 100 | 99 | 100 | 100 |
| –(phenyl)–CF₃ (meta) (prior art) | 0.5 | 21 | 89 | 87 | 17 | 97 | 90 |

0 = no damage
100 = plants destroyed

TABLE 5

Selective control of Galeopsis spp.; postemergence treatment in the greenhouse

Structure: R¹-substituted 4H-3,1-benzoxazine with C=O, O, N=C-R²

| R¹ | R² | Appln. rate [kg/ha] | Hordeum vulgare | Triticum aestivum | Galeopsis spp. |
|---|---|---|---|---|---|
| H | –(phenyl)–OCF₃ (meta) | 0.5 | 0 | 10 | 90 |
| H | –(phenyl)–OCF₃ (meta) | 1.0 | 0 | 10 | 94 |
| H | –(phenyl)–CF₃ (meta) (prior art) | 0.5 | 0 | 20 | 30 |
| H | –(phenyl)–CF₃ (meta) (prior art) | 1.0 | 0 | 23 | 40 |

TABLE 6

Selective herbicidal action of 4H-3,1-benzoxazine derivatives; postemergence treatment in the greenhouse Structure: R¹-substituted 4H-3,1-benzoxazine with C=O, O, N=C-R²

| R¹ | R² | Appln. rate [kg/ha] | Avena sativa | Centaurea spp. |
|---|---|---|---|---|
| F | –(phenyl) | 3.0 | 0 | 100 |
| Cl | –(phenyl)–OCF₃ (para) | 3.0 | 0 | 100 |
| Cl | –(phenyl)–OCF₃ (meta) | 3.0 | 0 | 100 |
| H | –(phenyl)–OCHF₂ (meta) | 3.0 | 20 | 70 |
| H | –(phenyl)–SCF₃ (meta) | 3.0 | 40 | 100 |
| H | –(phenyl)–SO₂CF₃ (meta) | 3.0 | 80 | 90 |
| H | –(cyclohexyl)–CH₃ | 3.0 | 0 | 100 |
| H | –(phenyl)–OCCl₃ (meta) | 3.0 | 40 | 90 |
| H | –CH₂–(phenyl)–CF₃ (meta) | 3.0 | 80 | 100 |

TABLE 6-continued

Selective herbicidal action of 4H-3,1-benzoxazine derivatives; postemergence treatment in the greenhouse ![structure]

| | | | Test plants and % damage | |
|---|---|---|---|---|
| R¹ | R² | Appln. rate [kg/ha] | Avena sativa | Centaurea spp. |
| H | (2,5-dimethylfuran) | 3.0 | 0 | 80 |

TABLE 7

Control of broadleaved weeds in cereals; postemergence treatment in the greenhouse ![structure]

| | | Test plants and % damage | | | | | | |
|---|---|---|---|---|---|---|---|---|
| R¹ | Appln. rate [kg/ha] | Hordeum vulgare | Oryza sativa | Triticum aestivum | Chenopod. album | Chrysanth. segetum | Matricaria spp. | Mercurialis annua |
| F | 1.0 | 0 | 0 | 0 | 90 | 100 | 99 | 98 |
| Cl | 1.0 | 0 | 6 | 7 | 40 | 50 | 75 | 58 |
| H (prior art) | 1.0 | 0 | 0 | 0 | 80 | 10 | 0 | 0 |

0 = no damage
100 = plants destroyed

TABLE 8

Selective control of unwanted plants; postemergence treatment in the greenhouse

![structure]

| | | | Test plants and % damage | | | | | | | |
|---|---|---|---|---|---|---|---|---|---|---|
| R¹ | R⁶ | Appln. rate [kg/ha] | Zea mays | Chenop. album | Desmod. tort. | Euphorb. genic. | Matric. spp. | Mercurial. annua | Malva neglecta | Solanum nigrum |
| H | —OCF₂CF₃ | 0.5 | 0 | 100 | 100 | 100 | 100 | 100 | 100 | 100 |
| F | —OCF₂CF₂H | 0.5 | 3 | 100 | 100 | 100 | 100 | 100 | 100 | 100 |
| Cl | —OCF₃ | 1.0 | 9 | 67 | 92 | 84 | 85 | 45 | 100 | 88 |
| H | —OCF₂CFHCL | 0.5 | 0 | 99 | 100 | 98 | — | 90 | — | 95 |

0 = no damage
100 = plants destroyed

TABLE 9

Control of unwanted plants in cotton; postemergence treatment in the greenhouse

![structure]

| | | Test plants and % damage | | | | | | | |
|---|---|---|---|---|---|---|---|---|---|
| R⁶ | Appln. rate [kg/ha] | Gossyp. hirs. | Acanthosp. hisp. | Chenop. alb. | Datura stram. | Euphorb. gen. | Solan. nigr. | Xanthium pens. | Sesbania exalt. |
| SO₂CF₃ | 1.0 | 0 | 100 | 87 | 100 | 79 | 93 | 100 | 73 |
| CF₃ | 1.0 | 43 | 100 | 97 | 80 | 26 | 99 | 99 | 67 |

0 = no damage
100 = plants destroyed

TABLE 10

Selective control of weeds in sugarbeets;
postemergence treatment in the greenhouse

[Structure: benzene ring with R¹ substituent, C(=O)-O-C(=CR²)-N forming a 4H-3,1-benzoxazine]

| R¹ | R² | Appln. rate kg/ha | Beta vulg. | Cheno-podium album | Solanum nigrum |
|---|---|---|---|---|---|
| H | phenyl-OCHF₂ | 2.0 | 10 | 85 | 100 |
| H | phenyl-Cl, OCF₂Cl | 2.0 | 8 | 88 | — |
| Cl | phenyl-OCF₂CHF₂ | 1.0 | 3 | 67 | 100 |
| F | phenyl-OCHF₂ | 1.0 | 0 | 100 | 100 |
| Cl | phenyl-OCHF₂ | 1.0 | 0 | 85 | 100 |

0 = no damage
100 = plants destroyed

In view of the good tolerance by the crop plants and the many application methods possible, the agents according to the invention, or mixtures containing them, may be used not only on the crop plants listed in the tables, but also in a much larger range of crops for removing unwanted plants. The application rates vary from 0.1 to 15 kg/ha and more.

The following crop plants may be mentioned by way of example:

| Botanical name | Common name |
|---|---|
| Allium cepa | onions |
| Ananas comosus | pineapples |
| Arachis hypogaea | peanuts (groundnuts) |
| Asparagus officinalis | asparagus |
| Avena sativa | oats |
| Beta vulgaris spp. altissima | sugarbeets |
| Beta vulgaris spp. rapa | fodder beets |
| Beta vulgaris spp. esculenta | table beets, red beets |
| Brassica napus var. napus | rape |
| Brassica napus var. napobrassica | |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Burmudagrass in turf and lawns |
| Daucus carota | carrots |
| Elais guineensis | oil palms |
| Fragaria vesca | strawberries |
| Glycine max | soybeans |
| Gossypium hirsutum (Gossypium arboreum Gossypium herbaceum Gossypium vitifolium) | cotton |
| Helianthus annuus | sunflowers |
| Helianthus tuberosus | |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicothiana tabacum (N. rustica) | tobacco |
| Olea europaea | olive trees |
| Oryza sativa | rice |
| Panicum miliaceum | |
| Phaseolus lunatus | limabeans |
| Phaseolus mungo | mungbeans |
| Phaseolus vulgaris | snapbeans, green beans, dry beans |
| Pennisetum glaucum | |
| Petroselinum crispum ssp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | |
| Ricinus communis | |
| Saccharum officinarum | sugar cane |
| Secale cereale | rye |
| Sesamum indicum | sesame |
| Solanum tuberosum | Irish potatoes |
| Sorghum bicolor (s. vulgare) | grain sorghum |
| Sorghum dochna | |
| Spinacia oleracea | spinich |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

The 4H-3,1-benzoxazine derivatives of the formula I may be mixed with each other, or with numerous representatives of other herbicidal or growth-regulating active ingredient groups, and applied in such combinations. These combinations extend the spectrum of action, and synergistic effects are sometimes achieved. Examples of compounds which may be admixed are diazines, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, etc. A number of active ingredients which, together with the new compounds, give mixtures useful for widely varying applications are listed below by way of example.

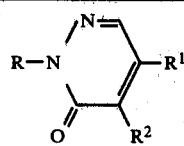

| R | R¹ | R² |
|---|---|---|
| phenyl- | NH₂ | Cl |
| phenyl- | NH₂ | Br |
| phenyl- | OCH₃ | OCH₃ |
| phenyl- | N(CH₃)₂ | Cl |
| cyclohexyl(H)- | OCH₃ | OCH₃ |
| cyclohexyl(H)- | NH₂ | Cl |
| 3-CF₃-phenyl- | N(CH₃)₂ | Cl |
| 3-CF₃-phenyl- | NHCH₃ | Cl |
| 3-CF₃-phenyl- | OCH₃ | Cl |
| cyclohexyl(H)- | NH₂ | Br |
| 3-CF₃-phenyl- | OCH₃ | OCH₃ |
| 3-F₂CHCF₂O-phenyl- | NHCH₃ | Cl |

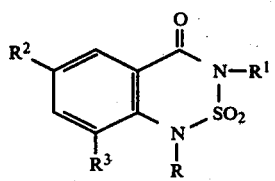

| R | R¹ | R² | R³ |
|---|---|---|---|
| H | i-C₃H₇ | H | H (salts) |
| H | i-C₃H₇ | H | CH₃ (salts) |
| H | i-C₃H₇ | H | Cl (salts) |
| CH₂—OCH₃ | i-C₃H₇ | H | H |
| H | i-C₃H₇ | H | F (salts) |
| CH₂—OCH₃ | i-C₃H₇ | H | Cl |
| CH₂—OCH₃ | i-C₃H₇ | H | F |
| CN | i-C₃H₇ | H | Cl |

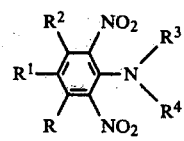

-continued

| R | R¹ | R² | R³ | R⁴ |
|---|---|---|---|---|
| H | H₃CSO₂ | H | n-C₃H₇ | n-C₃H₇ |
| H | F₃C | H | C₂H₅ | C₄H₉ |
| H | F₃C | H | n-C₃H₇ | n-C₃H₇ |
| H | F₃C | H | —CH₂—CH₂Cl | n-C₃H₇ |
| H | tert-C₄H₉ | H | sec-C₄H₉ | sec-C₄H₉ |
| H | SO₂NH₂ | H | n-C₃H₇ | n-C₃H₇ |
| H | F₃C | H | n-C₃H₇ | —CH₂—△ |
| H₃C | H₃C | H | H | sec-C₄H₉ |
| H₃C | H₃C | H | H | —CH(C₂H₅)₂ |
| H | F₃C | NH₂ | n-C₃H₇ | n-C₃H₇ |
| H | H₃C | H | n-C₃H₇ | n-C₃H₇ |
| H | i-C₃H₇ | H | n-C₃H₇ | n-C₃H₇ |

| R | R¹ | R² |
|---|---|---|
| Ph-CH₃ (tolyl) | H | i-C₃H₇ |
| 3-Cl-C₆H₄— | H | —CH₂—(3,4-diCl-C₆H₃) |
| 3-Cl-C₆H₄— | H | —CH(CH₃)—C≡CH |
| 3-Cl-C₆H₄— | H | —CH₂—C≡C—CH₂Cl |
| 3-Cl-C₆H₄— | H | i-C₃H₇ |
| C₆H₅— | H | —CH(CH₃)—C(O)—NH—C₂H₅ |
| 3,4-diCl-C₆H₃— | H | CH₃ |
| H₂N—C₆H₄—SO₂— | H | CH₃ |
| CH₃ | H | 2,6-di-tert-C₄H₉-4-CH₃-C₆H₂— |
| C₆H₅— | H | —N=C(CH₃)₂ |

| R | R¹ | R² |
|---|---|---|
| 3-CH₃-C₆H₄— | H | CH₃ |

-continued
| | | |
|---|---|---|
| 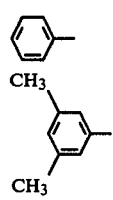 | H | C$_2$H$_5$ |
| 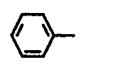 | H | C$_2$H$_5$ |
| 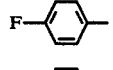 | CH$_3$ | CH$_3$ |
| 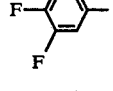 | H | CH$_3$ |
| 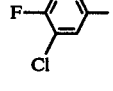 | H | C$_2$H$_5$ |
| 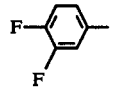 | H | C$_2$H$_5$ |
| 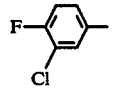 | H | CH$_3$ |
|  | H | CH$_3$ |
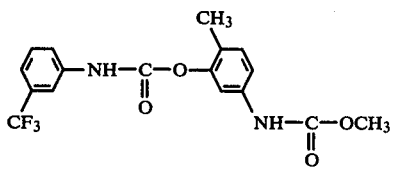
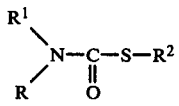
| R | R$^1$ | R$^2$ |
|---|---|---|
| i-C$_3$H$_7$ | i-C$_3$H$_7$ | —CH$_2$—CCl=CCl$_2$ |
| i-C$_3$H$_7$ | i-C$_3$H$_7$ | —CH$_2$—CCl=CHCl |
| n-C$_3$H$_7$ | n-C$_3$H$_7$ | C$_2$H$_5$ |
|  | C$_2$H$_5$ | C$_2$H$_5$ |
| sec-C$_4$H$_9$ | sec-C$_4$H$_9$ | C$_2$H$_5$ |
| n-C$_3$H$_7$ | n-C$_3$H$_7$ | n-C$_3$H$_7$ |
| C$_2$H$_5$ | C$_2$H$_5$ |  |
| sec-C$_4$H$_9$ | sec-C$_4$H$_9$ |  |
|  | C$_2$H$_5$ | C$_2$H$_5$ |
| i-C$_3$H$_7$ | i-C$_3$H$_7$ | 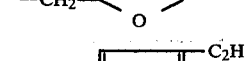 |
| i-C$_3$H$_7$ | i-C$_3$H$_7$ |  |

-continued
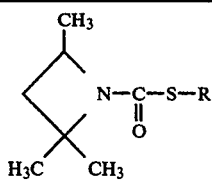
| R |
|---|
| —CH₂—CCl=CHCl |
| —CH₂—CCl=CCl₂ |
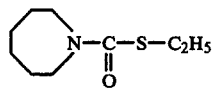
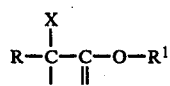
| R | X | Y | R¹ |
|---|---|---|---|
| CH₃ | Cl | Cl | Na |
|  | Cl | H | CH₃ |
| Cl—C₆H₄—CH₂— |  |  |  |
| C₆H₅—C(O)—NH—O— | H | H | H (salts) |
| Cl | Cl | Cl | Na |
| 2,4-Cl₂-C₆H₃—O—C₆H₄—O— | H | CH₃ | CH₃ |
| C₆H₅—C(O)—N(CH₃)—(3,4-Cl₂-C₆H₃) | H | CH₃ | C₂H₅ |
| C₂H₅ | Cl | Cl | Na |
| C₆H₅—C(O)—N(CH₃)—(3-Cl-4-F-C₆H₃) | H | CH₃ | i-C₃H₇ |
| C₆H₅—C(O)—N(CH₃)—(3-Cl-4-F-C₆H₃) | H | CH₃ | CH₃ |
| 4-Cl-C₆H₄—O—C₆H₄—O— | H | CH₃ | —CH₂—CH(CH₃)₂ |
| 3,5-Cl₂-pyridin-2-yl—O—C₆H₄—O— | H | CH₃ | Na |
| 4-CF₃-2-Cl-C₆H₃—O—C₆H₄—O— | H | CH₃ | Na |
| 4-CF₃-C₆H₄—O—C₆H₄—O— | H | CH₃ | CH₃ |

-continued

Structure: triazine with X at top carbon, R¹/R on one N-C-N branch, R²/R³ on other N-C-N branch

| R | R¹ | X | R² | R³ |
|---|---|---|---|---|
| H | tert-C₄H₉ | SCH₃ | H | C₂H₅ |
| H | C₂H₅ | SCH₃ | H | C₂H₅ |
| H | i-C₃H₇ | SCH₃ | H | C₂H₅ |
| H | CH₃ | SCH₃ | H | i-C₃H₇ |
| H | i-C₃H₇ | Cl | H | C₂H₅ |
| H | i-C₃H₇ | Cl | H | cyclopropyl |
| H | C₂H₅ | Cl | H | C₂H₅ |
| H | C₂H₅ | Cl | H | -C(CH₃)₂-CN |
| H | i-C₃H₇ | Cl | H | i-C₃H₇ |
| H | i-C₃H₇ | OCH₃ | H | i-C₃H₇ |
| H | NC-C(CH₃)₂- | Cl | H | cyclopropyl |
| H | C₂H₅ | Cl | H | -CH(CH₃)-CH₂-OCH₃ |
| H | C₂H₅ | Cl | H | -CH(CH₃)-C≡CH |

Structure: R¹R-N-C(=O)-R²

| R | R¹ | R² |
|---|---|---|
| CH₃ | CH₃ | CH(C₆H₅)₂ |
| 1-naphthyl | H | 2-COOH-phenyl |
| 3,4-dichlorophenyl | H | cyclopropyl |
| 3,4-dichlorophenyl | H | C₂H₅ |
| 5-chloro-4-methylthiazol-2-yl | H | C₂H₅ |
| 4-chlorophenyl | H | -C(CH₃)₂-CH₂-CH₂-CH₃ |
| phenyl | -CH(CH₃)-C≡CH | CH₂Cl |
| 2,6-dimethyl-3-ethylphenyl (2-CH₃, 3-C₂H₅) | -CH(CH₃)-CH₂-OCH₃ | CH₂Cl |
| 2,6-diethylphenyl | -CH₂-OCH₃ | CH₂Cl |

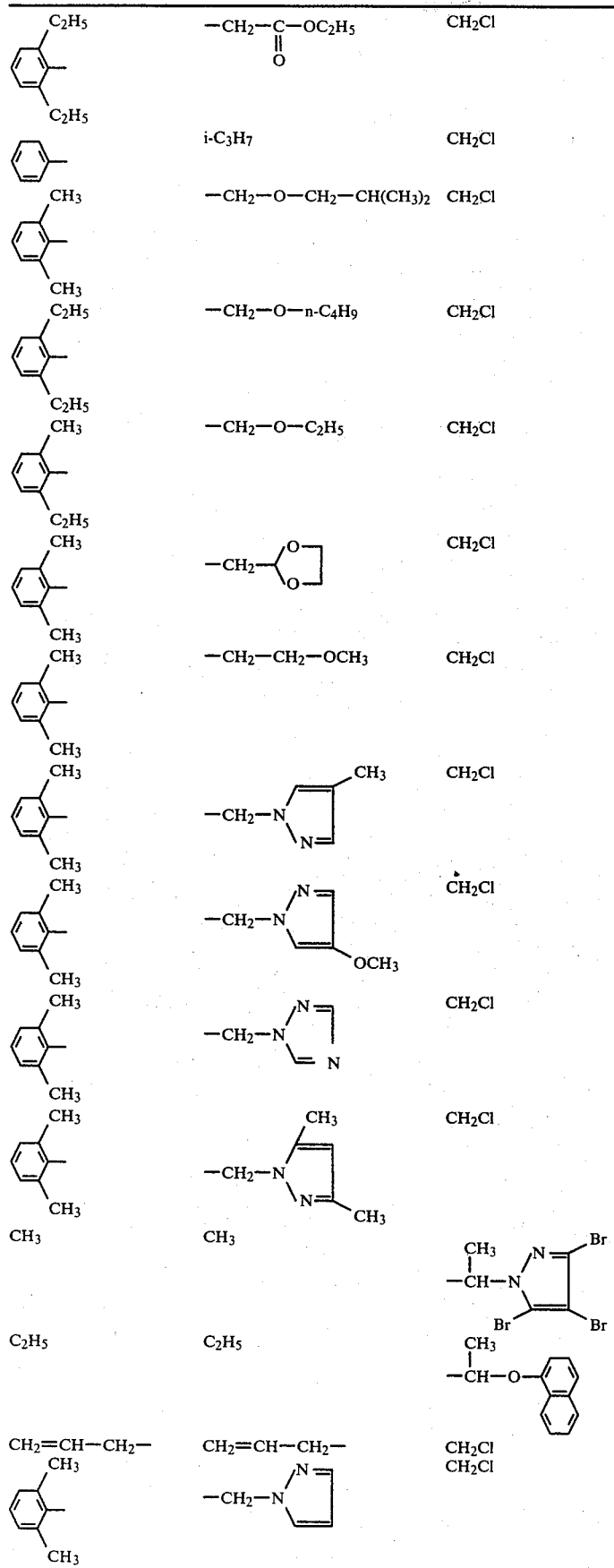

-continued
| | | |
|---|---|---|
| 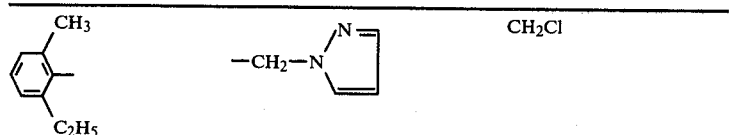 | —CH$_2$—N(pyrazole) | CH$_2$Cl |
| 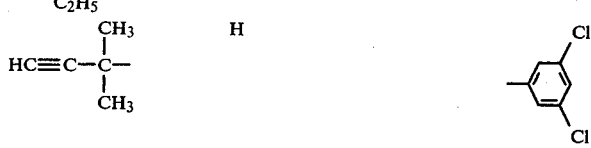 HC≡C—C(CH$_3$)$_2$— | H | 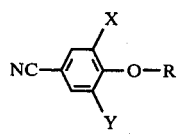 |
|  | H | CH$_3$ |
|  | H | CH$_3$ |
| X | Y | R |
|---|---|---|
| Br | Br | H (salts) |
| I | I | H (salts) |
| Br | Br | —C(=O)—(CH$_2$)$_6$—CH$_3$ |
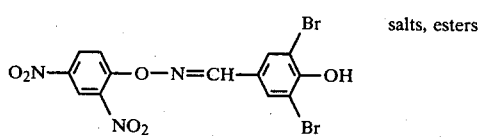 salts, esters
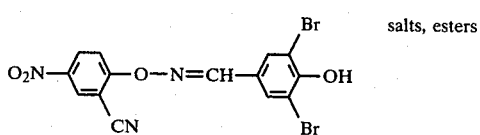 salts, esters
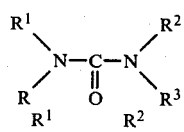
| R | R$^1$ | R$^2$ | R$^3$ |
|---|---|---|---|
| i-H$_7$C$_3$—C$_6$H$_4$— | H | CH$_3$ | CH$_3$ |
|  | H | CH$_3$ | CH$_3$ |
|  tert-H$_9$C$_4$—HN—C(=O)— | H | CH$_3$ | CH$_3$ |
| 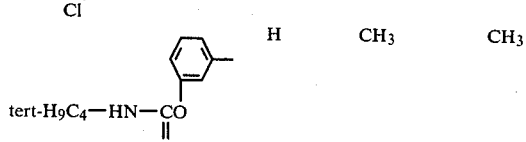 benzothiazol-2-yl | H | CH$_3$ | H |
|  benzothiazol-2-yl | CH$_3$ | CH$_3$ | H |
|  Cl—C$_6$H$_4$—O—C$_6$H$_4$— | H | CH$_3$ | CH$_3$ |

-continued

| Ar | R1 | R2 | R3 |
|---|---|---|---|
| 3,4-diCl-C6H3- | H | CH3 | CH3 |
| C6H5- | H | cyclohexyl-CH3 | H |
| 3-F3C-C6H4- | H | CH3 | CH3 |
| 4-Cl-C6H4- | H | CH3 | -CH(CH3)-C≡CH |
| 4-Br-C6H4- | H | CH3 | OCH3 |
| 3-CH3-4-Cl-C6H3- | H | CH3 | CH3 |
| 4-CH3-C6H4- | H | -C(CH3)2-C6H5 | H |
| 4-Cl-C6H4- | H | CH3 | OCH3 |
| 3-Cl-4-(ClF2CS)-C6H3- | H | CH3 | CH3 |
| C6H5- | H | CH3 | CH3 |
| 4-Cl-C6H4- | H | CH3 | CH3 |
| cycloheptyl- | H | CH3 | CH3 |
| 3,4-diCl-C6H3- | H | CH3 | OCH3 |
| 3-Cl-4-Br-C6H3- | H | CH3 | OCH3 |
| 3,4-diCl-C6H3- | H | CH3 | H |
| 2-tert-C4H9-5-thiadiazolyl | CH3 | CH3 | H |
| 2-CF3-5-thiadiazolyl | CH3 | CH3 | H |
| 3,4-diCl-C6H3- | H | C2H5 | C2H5 |
| 3-(F2CHCF2O)-C6H4- | H | CH3 | CH3 |

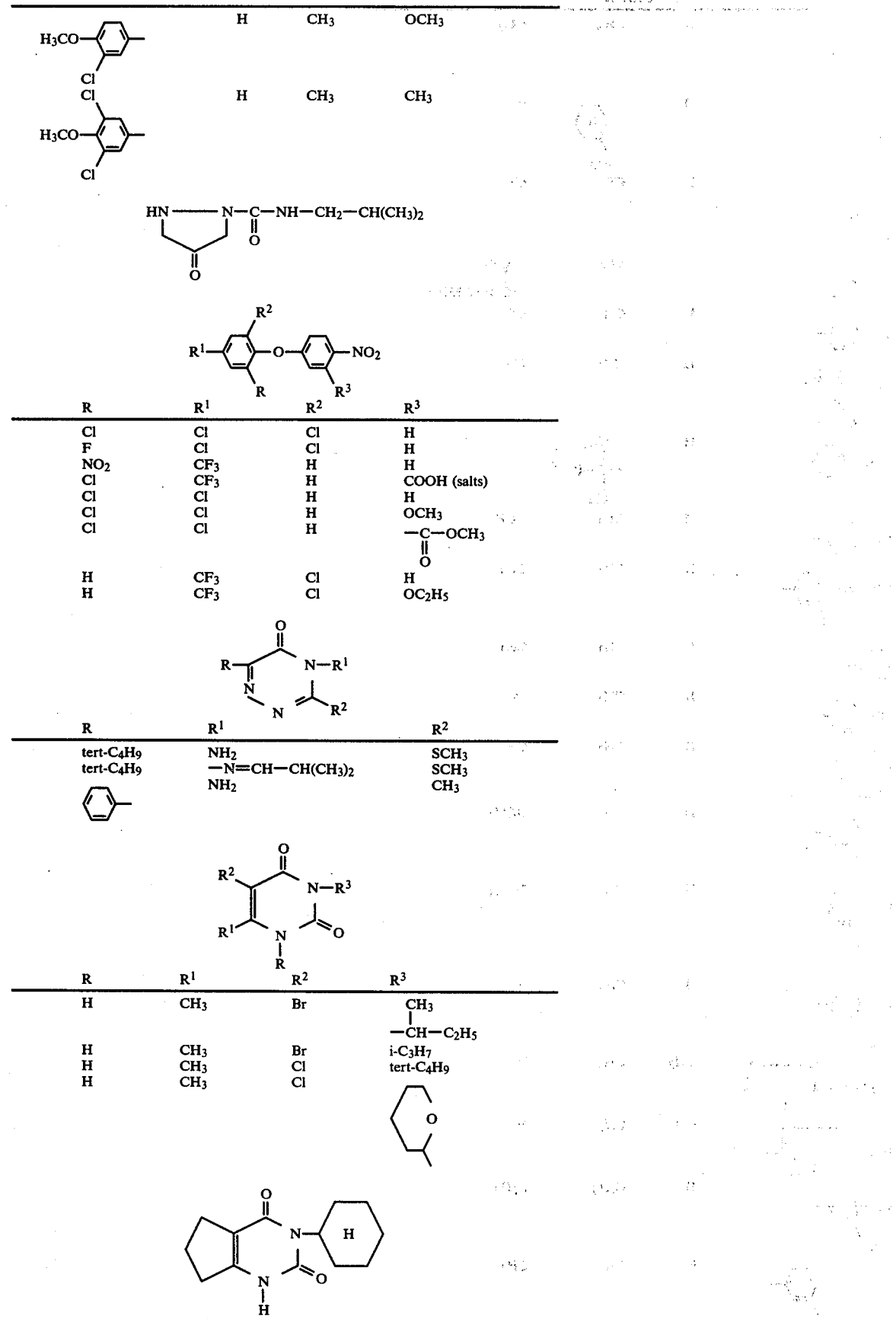

-continued
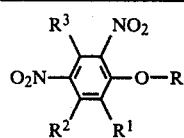
| R | R¹ | R² | R³ |
|---|---|---|---|
| —C(=O)—CH₃ | sec-C₄H₉ | H | H |
| H | CH₃ | H | H (salts, esters) |
| H | sec-C₄H₉ | H | H (salts, esters) |
| —C(=O)—CH₃ | tert-C₄H₉ | H | H |
| —C(=O)—CH₃ | tert-C₄H₉ | H | CH₃ |
| H | i-C₃H₇ | CH₃ | H (salts, esters) |
| H | tert-C₄H₉ | H | H (salts) |
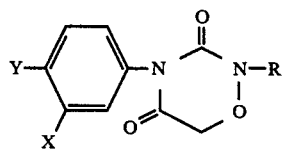
| X | Y | R |
|---|---|---|
| CF₃ | H | CH₃ |
| H | F | CH₃ |
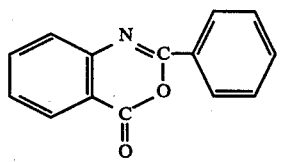
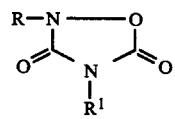
| R | R¹ |
|---|---|
| CH₃ | C₂H₅ |
| (H₃C)₂N— | C₂H₅ |
| (H₃C)(H₃C—C(=O))N— | C₂H₅ |
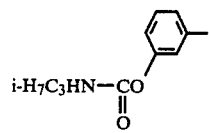
| R | R¹ |
|---|---|
| 3,4-dichlorophenyl | CH₃ |
| 3-(i-C₃H₇NH—C(=O)—O)phenyl | CH₃ |

-continued
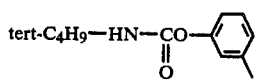  CH₃
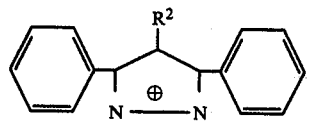
| R | R¹ | R² | X |
|---|----|----|---|
| CH₃ | CH₃ | H | 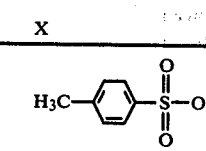 |
| CH₃ | CH₃ | Br | CH₃OSO₂O |
| CH₃ | CH₃ | CH₃ | CH₃OSO₂—O |
| CH₃ | CH₃ | CH₃ | CF₃—SO₂ |
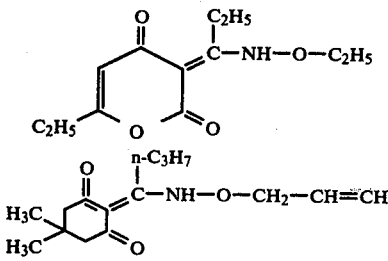
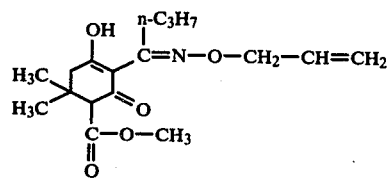
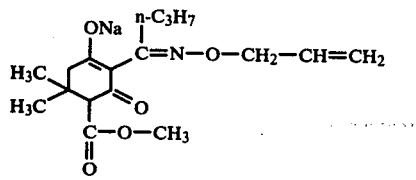
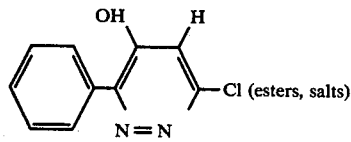 (esters, salts)
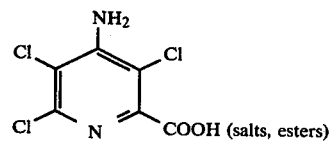 COOH (salts, esters)
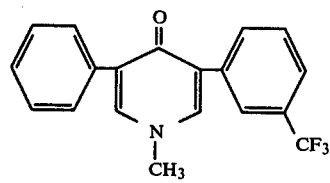

-continued
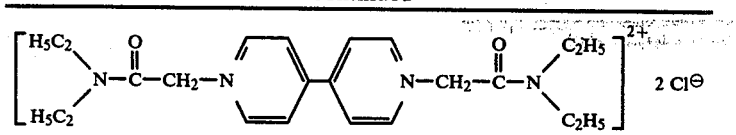
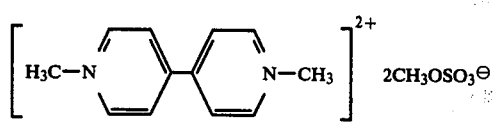
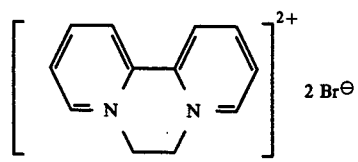
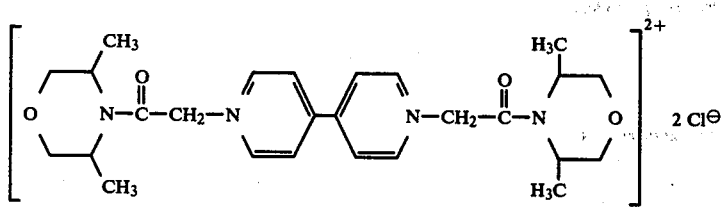
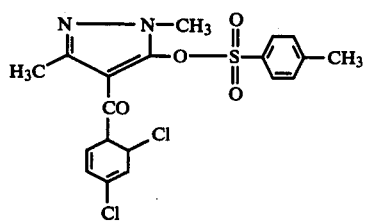
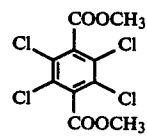
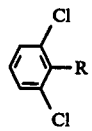
| R |
|---|
| CN |
| CSNH$_2$ |
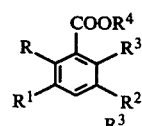
| R | R$^1$ | R$^2$ | R$^3$ | R$^4$ |
|---|---|---|---|---|
| H | Cl | NH$_2$ | Cl | (salts, esters, amides) |
| Cl | Cl | H | Cl | Na |
| H | I | I | I | H |
| Cl | H | Cl | OCH$_3$ | H |
| Cl | Cl | H | Cl | (CH$_3$)$_2$NH$_2$ |
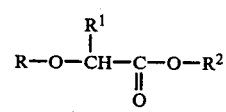
| R | R$^1$ | R$^2$ |
|---|---|---|

-continued
| | | |
|---|---|---|
| 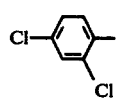 | CH₃ | H (salts, esters, amides) |
| 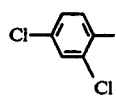 | H | H (salts, esters, amides) |
| 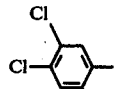 | H | H (salts, esters, amides) |
| 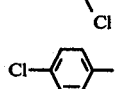 | H | H (salts, esters, amides) |
| 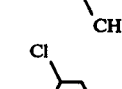 | CH₃ | H (salts, esters, amides) |
| 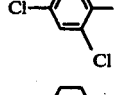 | CH₃ | H (salts, esters, amides) |
| 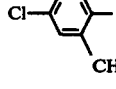 | CH₃ | H (salts, esters, amides) |
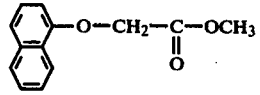
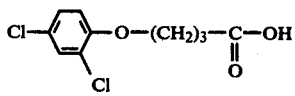 (salts, esters, amides)
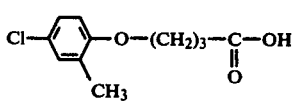 (salts, esters, amides)
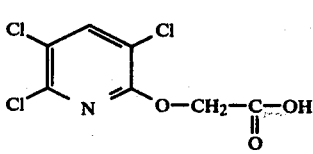 (salts, esters, amides)
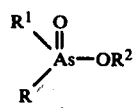
| R | R¹ | R² |
|---|---|---|
| OH | CH₃ | Na |
| CH₃ | CH₃ | Na |
| CH₃ | CH₃ | OH |
| ONa | CH₃ | Na |
$$R-N(R^1)-C(=O)-CH_2-O-S(=O)_2-R^2$$
| R | R¹ | R² |
|---|---|---|
| 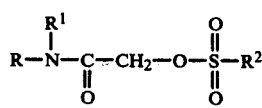 | —CH₂—O—C₂H₅ | CH₃ |

-continued
| | | |
|---|---|---|
| 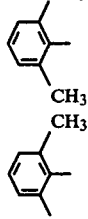 2,6-(CH₃)₂-C₆H₃ | i-C₃H₇—O—CH₂— | CH₃ |
|  2,6-(CH₃)₂-C₆H₃ | —CH₂—O—C₂H₅ | CH₃ |
| C₆H₅— | i-C₃H₇ | —NHCH₃ |
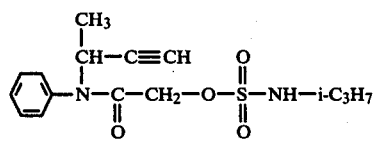
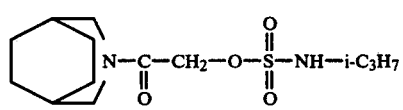
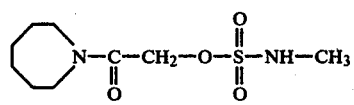
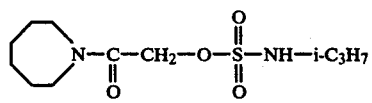
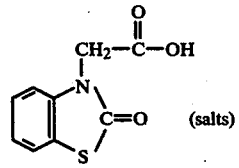 (salts)
 (salts, esters)
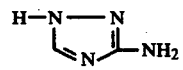
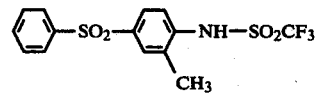
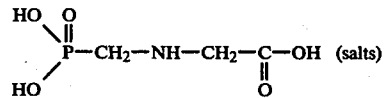 (salts)
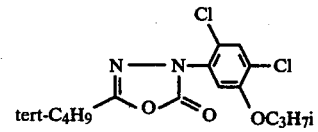
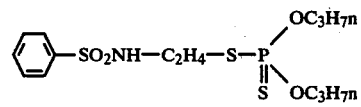

-continued
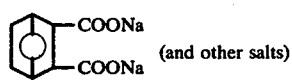 (and other salts)
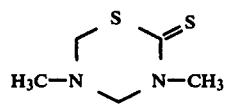
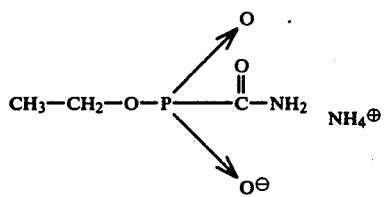 NH$_4^\oplus$
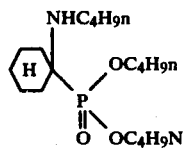
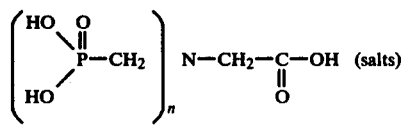 (salts)
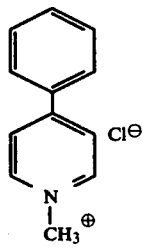
NH$_4$SCN
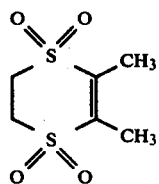
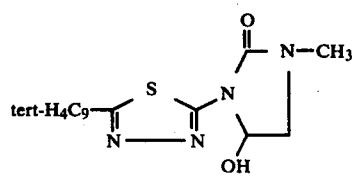
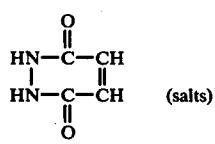 (salts)
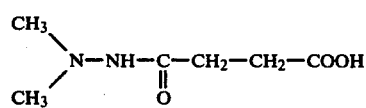

-continued

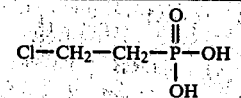

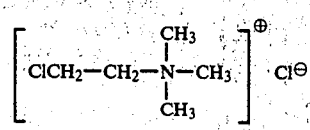

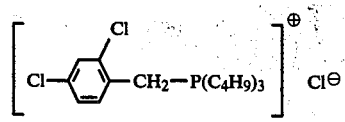

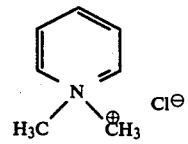

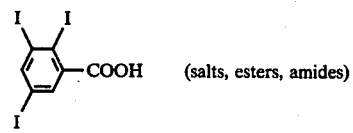   (salts, esters, amides)

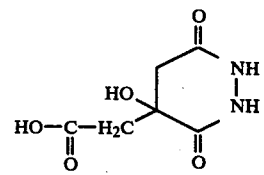

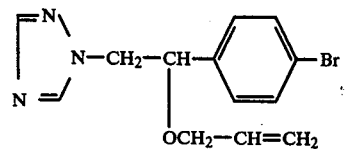

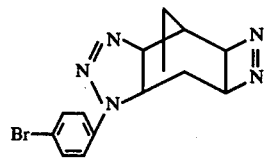

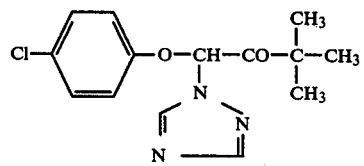

It may also be useful to apply the new compounds, either alone or in combination with other herbicides, in admixture with other crop protection agents, e.g., agents for combating pests or phytopathogenic fungi or bacteria. The compounds may also be mixed with solutions of mineral matters used to remedy nutritional or trace element deficiencies. It may also be advantageous to apply the compounds according to the invention (either on their own or in possible combinations) in admixture with solid or liquid mineral fertilizers.

We claim:
1. 4H-3,1-Benzoxazine derivatives of the formula

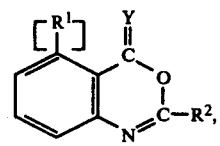

(I)

where

Y is oxygen or sulfur, $Ar(R^6)_n$, Ar denoting phenyl, $R^6$ denoting haloalkoxy or haloalkylmercapto, each of 1 to 4 carbon atoms, and n being 1 or 2.

2. 2-(p-Trifluoromethoxy-phenyl)-3,1-benzoxazin-4-one.

3. 2-(m-Trifluoromethoxy-phenyl)-3,1-benzoxazin-4-one.

4. 2-(m-1',1',2',2'-Tetrafluoroethoxy-phenyl)-3,1-benzoxazin-4-one.

5. A herbicide comprising a solid and/or liquid inert carrier and a 4H-3,1-benzoxazine derivative of the formula I as claimed in claim 1.

6. A process for combating unwanted plant growth, wherein the plants or the soil are treated with a herbicidally effective amount of a 4H-3,1-benzoxazine derivative of the formula I as claimed in claim 1.

7. A compound as set forth in claim 1 wherein n is 1.

8. 2-(m-chlorodifluoromethoxy-phenyl)-3,1-benzoxazin-4-one.

9. 2-(m-trifluoromethylmercapto-phenyl)-3,1-benzoxazin-4-one.

10. 2-(m-chlorodifluoromethylmercapto-phenyl)-3,1-benzoxazin-4-one.

* * * * *

UNITED STATES PATENT AND TRADEMARK OFFICE
CERTIFICATE OF CORRECTION

PATENT NO. : 4,315,766
DATED : February 16, 1982
INVENTOR(S) : G. Hamprecht and B. Wuerzer It is certified that error appears in the above—identified patent and that said Letters Patent is hereby corrected as shown below:

Page 1, under "Foreign Patent Documents" heading, change the third foreign patent document number "1670375" to read --1670350--.

IN THE CLAIMS:

Claim 1, column 78, line 63, change formula I

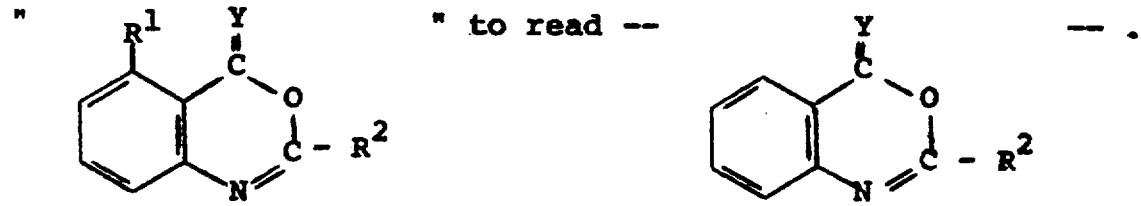

Signed and Sealed this

Twentieth Day of July 1982

[SEAL]

Attest:

GERALD J. MOSSINGHOFF

Attesting Officer     Commissioner of Patents and Trademarks